(12) United States Patent
Bojsen et al.

(10) Patent No.: US 8,679,774 B2
(45) Date of Patent: Mar. 25, 2014

(54) LIPOLYTIC ENZYME VARIANTS

(75) Inventors: Kirsten Bojsen, Hellerup (DK); Allan Svendsen, Horsholm (DK); Claus Crone Fuglsang, Niva (DK); Shamkant Anant Patkar, Lyngby (DK); Kim Borch, Birkerod (DK); Jesper Vind, Lyngby (DK); Andreas Petri, Copenhagen (DK); Sanne O. Schroder Glad, Ballerup (DK); Gitte Budolfsen, Frederiksberg (DK)

(73) Assignee: Novozymes A/S, Bagsvaerd (DK)

( * ) Notice: Subject to any disclaimer, the term of this patent is extended or adjusted under 35 U.S.C. 154(b) by 0 days.

(21) Appl. No.: 12/849,911

(22) Filed: Aug. 4, 2010

(65) Prior Publication Data

US 2010/0291262 A1    Nov. 18, 2010

Related U.S. Application Data

(60) Continuation of application No. 12/245,082, filed on Oct. 3, 2008, now Pat. No. 7,851,176, which is a division of application No. 11/951,597, filed on Dec. 6, 2007, now Pat. No. 7,632,669, which is a division of application No. 10/779,427, filed on Nov. 22, 2004, now Pat. No. 7,312,062, which is a division of application No. 09/856,819, filed as application No. PCT/DK99/00664 on Nov. 29, 1999, now abandoned.

(60) Provisional application No. 60/111,430, filed on Dec. 8, 1998, provisional application No. 60/126,914, filed on Mar. 29, 1999, provisional application No. 60/160,735, filed on Oct. 22, 1999.

(30) Foreign Application Priority Data

| Nov. 27, 1998 | (DK) | 1998 01572 |
| Mar. 22, 1999 | (DK) | 1999 00391 |
| Oct. 15, 1999 | (DK) | 1999 01481 |

(51) Int. Cl.
| C12Q 1/34 | (2006.01) |
| C12N 9/20 | (2006.01) |
| C12N 1/20 | (2006.01) |
| C12N 15/00 | (2006.01) |
| C07H 21/04 | (2006.01) |

(52) U.S. Cl.
USPC ....... 435/18; 435/198; 435/252.3; 435/320.1; 536/23.2

(58) Field of Classification Search
USPC .................. 435/198, 252.3, 320.1; 536/23.2
See application file for complete search history.

(56) References Cited

U.S. PATENT DOCUMENTS

| 2,527,786 A | 10/1950 | Armstrong |
| 3,368,903 A | 2/1968 | Johnson et al. |
| 4,567,046 A | 1/1986 | Inoue et al. |
| 5,264,367 A | 11/1993 | Aalrust et al. |
| 5,869,438 A * | 2/1999 | Svendsen et al. ............. 510/226 |
| 5,892,013 A | 4/1999 | Svendsen et al. |
| 5,965,422 A | 10/1999 | Loffler et al. |
| 5,976,855 A | 11/1999 | Svendsen et al. |
| 6,077,818 A | 6/2000 | Baeck et al. |
| 6,140,094 A | 10/2000 | Loffler et al. |
| 6,251,444 B1 | 6/2001 | Van Eijk et al. |
| 6,495,357 B1 * | 12/2002 | Fuglsang et al. ............. 435/198 |
| 6,866,687 B2 | 3/2005 | Batchelor |
| 7,056,544 B2 | 6/2006 | Xu et al. |

FOREIGN PATENT DOCUMENTS

| EP | 109244 | 4/1987 |
| EP | 0 258 068 | 3/1988 |
| EP | 0 260 105 | 5/1994 |
| EP | 0 943 678 | 9/1999 |
| EP | 0 869 167 B1 | 10/2002 |
| EP | 2 119 781 A1 | 11/2009 |
| EP | 2 156 750 A1 | 2/2010 |
| FR | 2359624 | 2/1978 |
| GB | 1133533 | 11/1968 |
| JP | 63240755 | 10/1988 |
| JP | 5041991 | 2/1993 |
| JP | 7231788 | 9/1995 |
| JP | 10155493 | 6/1998 |
| JP | 63240755 | 10/1998 |
| WO | WO 92/05249 * | 4/1992 |
| WO | WO 94/01541 | 1/1994 |
| WO | WO 94/04035 A1 | 3/1994 |
| WO | WO 94/25577 | 11/1994 |
| WO | WO 95/09909 | 4/1995 |
| WO | WO 95/22614 | 8/1995 |
| WO | WO 95/22615 | 8/1995 |
| WO | WO 95/35381 | 12/1995 |
| WO | WO 96/16153 | 5/1996 |
| WO | WO 96/18729 | 6/1996 |

(Continued)

OTHER PUBLICATIONS

Atomi et al, Microbial Lipases Conference Paper 2 pages (1995).
Brzozowski et al, Letters to Nature, vol. 351, pp. 491-494 (1991).
Wooley et al, Lipases their structure biochemistry and application, pp. 1-21 (1994).
Scheib et al, Protein Engineering, vol. 11, No. 8, pp. 675-682 (1998).
Acker et al, Getreide Mehl Brot, vol. 28, pp. 181-187 (1974).
Bachmatova et al, Biologija, Part 1 and 2 pp. 57-59 (1995).
Brady et al, Nature, vol. 343, pp. 767-770 (1990).
Derewenda et al, Biochemistry, vol. 31, pp. 1532-1541 (1992).
Eliasson et al, Physicochemical Behavior of Components Chapter 2, "Cereals in Breadmaking", pp. 29-45 (1993).

(Continued)

*Primary Examiner* — Tekchand Saidha
(74) *Attorney, Agent, or Firm* — Kristin J. McNamara

(57) ABSTRACT

The substrate specificity of a lipolytic enzyme can be modified by making alterations to the amino acid sequence in a defined region of the lipolytic enzyme, so as to increase the level of a desired activity or to decrease the level of an undesired activity. Thus, the inventors have developed lipolytic enzyme variants with a modified amino acid sequence with a substrate specificity which can be tailored for specific uses.

36 Claims, 1 Drawing Sheet

(56) References Cited

FOREIGN PATENT DOCUMENTS

| WO | WO 97/04078 | 2/1997 |
|---|---|---|
| WO | WO 97/04079 | 2/1997 |
| WO | WO 97/07202 | 2/1997 |
| WO | WO 97/07205 | 2/1997 |
| WO | WO 97/30148 | 8/1997 |
| WO | WO 98/08939 | 3/1998 |
| WO | 98/14594 A2 | 4/1998 |
| WO | WO 98/14594 | 4/1998 |
| WO | WO 98/26057 | 6/1998 |
| WO | WO 98/41653 | 9/1998 |
| WO | 98/44804 A1 | 10/1998 |
| WO | WO 98/45453 | 10/1998 |
| WO | WO 99/49011 | 3/1999 |
| WO | WO 99/42566 | 8/1999 |
| WO | WO 99/53769 | 10/1999 |
| WO | WO/00/60063 A1 | 10/2000 |
| WO | WO 01/72783 A2 | 10/2001 |
| WO | WO 02/00852 A2 | 1/2002 |
| WO | WO 2005/087918 A2 | 9/2005 |
| WO | WO 2009/106575 A1 | 9/2009 |

OTHER PUBLICATIONS

Frenken et al, Applied and Environmental Microbiology, vol. 58, (12), pp. 3787-3791 (1992).
Gant et al, Journal of Cereal Science, vol. 18, pp. 207-210, (1993).
Hara et al, JAOCS, "Reaction of Phosphtidycholine", vol. 74, No. 9, (1997).
Henderson et al, Journal of Lipid Research, vol. 34, pp. 1593-1602 (1993).
Hjort et al, Biochemistry, vol. 32, pp. 4702-4707 (1993).
Holmquist et al, Journal of Protein Chemistry, vol. 14 No. 4, pp. 217-224 (1995).
Holmquist et al, Lipids, vol. 29, No. 9, pp. 599-603 (1994).
Holmquist et al, Journal of Protein Chemistry, vol. 12, No. 6, pp. 749-757 (1993).
Joerger et al, Lipids, vol. 29, No. 6, pp. 377-384 (1994).
Kampen et al, Chemistry and Physics of Lipids, vol. 93, pp. 39-45 (1998).
Klein et al, JAOCS, vol. 74, No. 11, pp. 1401-1407 (1997).
Klein et al, Lipids, vol. 32, No. 2, pp. 123-130 (1997).
Kuipers et al, Science, vol. 244, pp. 82-85 (1989).
Marion et al, "Wheat Lipid-Binding Proteins: Structure and Function", (2000).
Marion et al, Interaction: The Keys to Cereal Quality, Chapter 6, Lipids, pp. 131-167 (1998).
Martinelle et al, Protein Engineering vol. 9, No. 6, pp. 519-524 (1996).
Murakami et al, Tetrahedron, vol. 50, No. 1, pp. 2003-2016 (1994).
Murakami et al, Tetrahedron, vol. 50, No. 7, pp. 1993-2002 (1994).
Norin et al, Protein Science, vol. 3, pp. 1493-1503 (1994).
Oils-Fats-Lipids 1995. 21$^{st}$. Oct 1995, The Hague vol. 1.
Peters et al, Biophysical Journal, vol. 71, pp. 119-129 (1996).
Peters et al, Biochemistry, vol. 37, pp. 12375-12383 (1998).
Poulsen et al, The First European Symposium on Enzymes and Grain Processing pp. 201-214 (1997).
Scheib et al, Protein Science, vol. 8, pp. 215-221 (1999).
Slideshow Presentation, "Effect & Functionality of Lipases in Dough and Bread" Santonini Congress, (1999).
Soumanou et al, JAOCS, vol. 75, No. 6, pp. 703-710 (1998).
Stadler et al, CCACAA 68 (3) pp. 649-674 (1995).
Stampfli et al, Food Chemistry, vol. 52, pp. 353-360 (1995).
Svendsen et al, Biotechnology, vol. 5, No. 5, pp. 619-623 (1994).
W. Van Nieuwenhuyzen IFI "Open Doors to Baked Goods" No. 2, pp. 32-36 (1998).
Novo Nordisk Analytical method AF 95/6-GB "Lipase/Esterase—pH-state Method on a Tributyrin Substrate (LU)," pp. 1-5 (Feb. 7, 1991).
Novozymes Letter dated Apr. 21, 2009 to the EPO discussed inventive step and including a declaration with supplementary data of Dr. Henrik Lundkvist, pp. 1-11.
IPER of Mar. 9, 2001, pp. 1-6.
Communication of EPO dated Dec. 19, 2007 to Novozymes, pp. 1-6.
Novozymes Letter dated Nov. 25, 2008 to the EPO discussed inventive step and including the (first) declaration with supplementary data of Dr. Henrik Lundkvist, pp. 1-6.
Svendsen et al., Methods in Enzymology, vol. 284, pp. 317-340 (1997).
Kanok-Orn Intarapichet, Suranaree J. Sci. Technol. vol. 3, pp. 21-29 (1996).
Christen et al., Food Biotechnology, vol. 8, No. 2 & 3, pp. 167-190 (1994).
Product sheet of Fermizyme L 80.000, pp. 1-4 (Oct. 13, 1997).
Product sheet of Novozym 677BG, pp. 1-2 (Apr. 1998).
Schonheyder et al., "On the Affinity of Pig Pancreas Lipase for Tricaproin in Heterogeneous Solution," From the Biochemical Institute, Aarhus University, Denmark, pp. 57-67 (1944).
Benzonana et al., Biochimica et Biophysica Acta, vol. 105, pp. 121-136 (1965).
Carriere, "Enzyme (Lipase) Assays: Pancreatic Enzyme Replacement Products," USP Bioassay Workshop Presentation, pp. 1-30 (Aug. 13-14, 2008).
Tiss et al., Analytical Biochemistry, vol. 294, pp. 36-43 (2001).
Greenough et al., Fd Chem. Toxic., vol. 34, No. 2, pp. 161-166 (1996).
Email regarding Sigma olive oil substrate 800-1, pp. 1-2 (Sep. 16, 2009).
Witness Statement of Dr Jan Metske van der Laan, pp. 1-8 (Jan. 12, 2009).
Curriculum Vitae Jan Metske van der Laan (=Exhibit JML-1 of D19), pp. 1-7 (Jan. 6, 2010).
Third Witness Statement of Dr. Jan Metske Van Der Laan, pp. 1-6 (Feb. 12, 2010).
Screen print of order (=Exhibit JML-3 of D22), pp. 1-4 (Jan. 6, 2010).
Confirmation letter (=Exhibit JML-4 of D22), p. 1 (Dec. 22, 2009).
WO2005/087918 (=Exhibit JML-6 of D22).
Andersson et al., Journal of Lipid Research, vol. 36, pp. 1392-1400 (1995) (=Exhibit JML-7 of D22).
Joint Witness Statement of Jan Metske Van Der Laan and Willem Bijleveld, pp. 1-25 (Jan. 12, 2009).
List of all exhibits for Joint Witness Statement of Jan Metske Van Der Laan and Willem Bijleveld, p. 1 (Jan. 6, 2010).
Curriculum Vitae Willem Bijleveld, pp. 1-2 (Jan. 6, 2010) (=Exhibit 2 of D28).
Timmermans et al, Biochem J. vol. 314, pp. 931-936 (1996) (=Exhibit 3 of D28).
Fernandez et al, Applied and Environmental Microbiology, vol. 66, No. 4, pp. 1360-1368 (2000) (=Exhibit 4 of D28).
Bertram et al, J Am Oil Chem Soc, vol. 85, pp. 47-53 (2008) (=Exhibit 5 of D28).
Food Chemicals Codex Fourth Edition, 2 pages, "Lipase Activity," p. 803 (effective Jul. 1, 1996) (=Exhibit 6 of D28).
DSM lipase activity protocol of Sep. 12, 2008, pp. 1-11 (=Exhibit 7 of D28).
DSM lipase activity protocol of Apr. 3, 2001, pp. 1-7 (Exhibit 8 of D28).
DSM lipase activity protocol of Dec. 13, 1999, pp. 1-3 (=Exhibit 9 of D28).
Titration plots, pp. 1-3 (=Exhibit 10 of D28).
Magnin et al, Journal of Bioactive and Compatible Polymers, pp. 355-373 (2003) (=Exhibit 12 of D28).
First Declaration of Henrik Ostdal, pp. 1-53 (Sep. 18, 2009).
English translation of part of Exhibit D41 (protocol "Lipase activity measured with SLU method"), pp. 1-8 (=Exhibit 15 of D28).
Second Joint Witness Statement of Jan Metske Van Der Laan and Willem Bijleveld, pp. 1-5 (Mar. 12, 2010).
Third Joint Witness Statement of Jan Metske Van Der Laan and Willem Bijleveld, pp. 1-3 (Mar. 24, 2010).
Order of Oct. 30, 2009 Geneart AG, pp. 1-4 (=Exhibit of D43).
Witness Statement of Prof. Dr. Maarten Edmond, pp. 1-41 (Mar. 23, 2010) including Curriculum Vitae Maarten Egmond and list of publications.
Email exchange with Dr. Rocha, pp. 1-3 (Jan. 29, 2010).
Witness Statement of Dr. Eduard P.P.A. Derks, pp. 1-13 (2010).

(56) References Cited

OTHER PUBLICATIONS

Meilgaard Civille Carr, Sensory Evaluation Techniques Third Edition, pp. 52-55 and 294-295 (1999) (=Exhibit of D47).
Harry T. Lawless et al, Sensory Evaluation of Food, Principles and Practices, pp. 216-225 (1999) (=Exhibit of D47).
Per Brun Brockhoff et al, Food Quality and Preference, pp. 1-9 (2009) (=Exhibit of D47).
Wakeling et al, Food Quality and Preferences vol. 6, pp. 299-308 (1995) (=Exhibit of D47).
Witness Statement of Professor Halliday J.H. Macfie, pp. 1-6 (Mar. 23, 2010).
Curriculum Vitae of Professor Halliday Macfie, pp. 1-5 (2010).
Second Declaration of Henrik Lundkvist, pp. 1-6 (Feb. 16, 2010).
Third Declaration of Henrik Lundkvist, pp. 1-7 (Mar. 31, 2010).
Certified English translation of D57, p. 1 (Jan. 7, 2010).
Declaration of Kim Howard Brauner Lund from the court proceedings in the Netherlands, pp. 1-9, (Feb. 12, 2010).
Second Declaration of Kim Howard Brauner Lund from the Court proceedings in the Netherlands, pp. 1-2 (Mar. 31, 2010).
Expert Report of Uwe Bornscheuer from the Court proceedings in the Netherlands, 14 pages (Feb. 11, 2010).
Exhibit 4 of D60, Takahashi et al, Journal of Fermentation and Bioengineering, vol. 86, No. 2, pp. 164-168 (1998).
Exhibit 6 of D60, Declaration of Henrik Lundkvist Apr. 21, 2009, pp. 1-8.
Exhibit 7 of D60, Schmidt-Dannert et al, Biochimica et Biophysica Acta vol. 1214, pp. 43-53 (1994).
Second Expert Report of Uwe Bornscheuer, pp. 1-22 (Mar. 16, 2010).
Declaration of Joseph Demeester and Appendices 1-2, pp. 1-30 (Jul. 9, 2010).
Arzoglou et al., Eur. J. Clin. Chem. Clin. Biochem., vol. 32, pp. 773-777 (1994) (=Appendix 3 of D72).
Demeester, "Lipases, measurement and substrate challenges," U.S.P. Enzyme Workshop, Jul. 8-9 2009, USP Headquarters, Rockville, pp. 1-12 (=Appendix 4 of D72).
Demeester et al. "Microbial Lipases (F.I.P.)" in Pharmaceutical Enzymes, pp. 343, 379-383 (1997) (=Appendix 5 of D72).
Demeester et al. "Lipolytic Activity" in Pharmaceutical Enzymes (1997) (=Appendix 6 of D72).
European Pharmacopoeia, "Pancreas Powder" Sixth Edition, vol. 2, pp. 2605-2607 (2007) (=Appendix 7 of D72).
United States Pharmacopeia, "Pancrelipase" USP 31, NF 26, vol. 1, p. 2908 (2008)(=Appendix 8 of D72).
Lipase (Microbial) Activity for Medium- and Long-chain Fatty Acids, FCC 7,pp. 1201-1202 (2010) (=Appendix 9 of D72).
Nagao et al, J Biochem, vol. 124, No. 6, pp. 1124-1129 (1998).
Fluka 62314 "Lipase Substrate: BioChemika for the titrimetric determination of enzyme activity", p. 1 (Undated).
Spectra (=Exhibit JML-2 of D19), pp. 1-3 (D19 dated Jan. 12, 2009).
EP2119781 (=Exhibit JML-5 of D22) (Nov. 18, 2009).
"Test results SLU and LU activity using the Fluka Substrate," p. 1 (=Exhibit 14 of D28) (D28 dated Jan. 12, 2009).
Rocha et al, "Triton X-100 as Emulsifier on the Lipolytic Activity Determination," pp. 1-6 (=Exhibit of D45) (D45 dated Mar. 23, 2010).
Pages 12/40 of the opponent's counterclaim in the Court proceedings in the Netherlands (Undated).
Exhibit 1 of D60, Leaflet describing the work carried out in the Bornscheuer Group, 3 pages (D60 dated Feb. 11, 2010).
Exhibit 2 of D60, Curriculum Vitae Professor Dr. Uwe Bornscheuer, 2 pages (D60 dated Feb. 11, 2010).
Exhibit 3 of D60, List of Professor Bornscheuer's papers from PhD studies, 2 pages (D60 dated Feb. 11, 2010).
Exhibit 5 of D60, List of Publications, Uwe Bornscheuer, pp. 1-20 (D60 dated Feb. 11, 2010).
English translation of D72, pp. 1-25 (D72 dated Jul. 9, 2010).
Carriere et al, Biochim et Biophy Acta, vol. 1376, pp. 417-432 (1998).
Letter from Kevin Doss, 1 page (Mar. 4, 2003).
Nagao et al., Genbank, Access No. AAB34680 (1994).
Yamaguchi et al., Genbank, Access No. BAA1434 (1991).
De Vries et al., Genbank, Access No. CAA70510 (1997).
De Vries et al., Genbank, Access No. CAA70511 (1997).
Isobe et al., Genbank, Access No. AAB26004 (1993).

\* cited by examiner

```
              1                                                              50
     rhimi    SIDGGIRAAT SQEINELTYY TTLSANSYCR TVIPGA...T WDC..IHCDA
     rhidl    SDGGKVVAAT TAQIQEFTKY AGIAATAYCR SVVPGN...K WDC..VQCQK
     SP400    ~~~~~~~EVS QDLFNQFNLF AQYSAAAYCG KNNDAPAGTN ITCTGNACPE
       Pcl    ~~~~~~~DVS TSELDQFEFW VQYAAASYYE ADYTAQVGDK LSCSKGNCPE
   FoLnp11    ~~~~~AVGVT TTDFSNFKFY IQHGAAAYC. .NSEAAAGSK ITCSNNGCPT 51                                                             100
     rhimi    TE..DLKIIK TWS.TLIYDT NAMVARGDSE KTIYIVFRGS SSIRNWIADL
     rhidl    WV.PDGKIIT TFT.SLLSDT NGYVLRSDKQ KTIYLVFRGT NSFRSAITDI
     SP400    VEKADATFLY SFEDSGVGDV TGFLALDNTN KLIVLSFRGS RSIENWIGNL
       Pcl    VEATGATVSY DFSDSTITDT AGYIAVDHTN SAVVLAFRGS YSVRNWVADA
   FoLnp11    VQGNGATIVT SFVG.SKTGI GGYVATDSAR KEIVVSFRGS INIRNWLTNL 101                                                            150
     rhimi    TFVPVSY.PP VSGTKVHKGF LDSYGEVQNE LVATVLDQFK QYPSYKVAVT
     rhidl    VFNFSDY.KP VKGAKVHAGF LSSYEQVVND YFPVVQEQLT AHPTYKVIVT
     SP400    NFDLKEINDI CSGCRGHDGF TSSWRSVADT LRQKVEDAVR EHPDYRVVFT
       Pcl    TFVHTNP.GL CDGCLAELGF WSSWKLVRDD IIKELKEVVA QNPNYELVVV
   FoLnp11    DFGQEDC.SL VSGCGVHSGF QRAWNEISSQ ATAAVASARK ANPSFNVIST 151                                                            200
     rhimi    GHSLGGATAL LCALDLYQRE EGLSSSNLFL YTQGQPRVGD PAFANYVVST
     rhidl    GHSLGGAQAL LAGMDLYQRE PRLSPKNLSI FTVGGPRVGN PTFAYYVEST
     SP400    GHSLGGALAT VAGADLRGN. .GY...DIDV FSYGAPRVGN RAFAEFLTVQ
       Pcl    GHSLGAAVAT LAATDLRGK. .GYP...SAKL YAYASPRVGN AALAKYITAQ
   FoLnp11    GHSLGGAVAV LAAANLRVG. .GT...PVDI YTYGSPRVGN AQLSAFVSNQ 201                                                            250
     rhimi    G.IPYRRTVN ERDIVPHLPP AAFGFLHAGE EYWITD.NSP ......ETVQ
     rhidl    G.IPFQRTVH KRDIVPHVPP QSFGFLHPGV ESWIKS.GT. ......SNVQ
     SP400    TGGTLYRITH TNDIVPRLPP REFGYSHSSP EYWIKS.GTL V.PVTRNDIV
       Pcl    G..NNFRFTH TNDPVPKLPL LSMGYVHVSP EYWITS.PNN A.TVSTSDIK
   FoLnp11    A.GGEYRVTH ADDPVPRLPP LIFGYRHTTP EFWLSGGGGD KVDYTISDVK 251                                                            300
     rhimi    VCTSDLETSD CSNSIVPFT. .SVLDHLSYF GINTGLCT~~ ~~~~~~~~~~
     rhidl    ICTSEIETKD CSNSIVPFT. .SILDHLSYF DINEGSCL~~ ~~~~~~~~~~
     SP400    KIEGID.ATG GNNQP.NIP. .DIPAHLWYF .GLIGTCL~~ ~~~~~~~~~~
       Pcl    VIDGDV.SFD GNTGTGLPLL TDFEAHIWYF .VQVDAGKGP GLPFKRV~~~
   FoLnp11    VCEGAA.NLG CNGGT.LGL. .DIAAHLHYF .QATDACNAG GFSWRRYRSA 301                                                            338
     rhimi    ~~~~~~~~~~ ~~~~~~~~~~ ~~~~~~~~~~ ~~~~~...
     rhidl    ~~~~~~~~~~ ~~~~~~~~~~ ~~~~~~~~~~ ~~~~~...
     SP400    ~~~~~~~~~~ ~~~~~~~~~~ ~~~~~~~~~~ ~~~~~...
       Pcl    ~~~~~~~~~~ ~~~~~~~~~~ ~~~~~~~~~~ ~~~~~...
   FoLnp11    ESVDKRATMT DAELEKKLNS YVQMDKEYVK NNQARS..
```

LIPOLYTIC ENZYME VARIANTS

CROSS-REFERENCE TO RELATED APPLICATIONS

This application is a continuation of U.S. application Ser. No. 12/245,082 filed on Oct. 3, 2008 (now U.S. Pat. No. 7,851,176) which is a divisional of U.S. application Ser. No. 11/951,597 filed on Dec. 6, 2007 (now U.S. Pat. No. 7,632,669), which is a divisional of U.S. application Ser. No. 10/779,427, filed Nov. 22, 2004 (now U.S. Pat. No. 7,312,062), which is a division of U.S. application Ser. No. 09/856,819, filed May 24, 2001 (now abandoned), which claims priority from application serial no. PCT/DK99/00664, filed on Nov. 29, 1999, which claims the benefit of U.S. application No. 60/111,430, filed Dec. 8, 1998, 60/126,914, filed Mar. 29, 1999, and 60/160,735, filed Oct. 22, 1999, and claims priority under 35 U.S.C. 119 of Danish application serial nos. PA 1998 01572, filed Nov. 27, 1998, PA 1999 00391, filed Mar. 22, 1999, and PA 1999 01481, filed Oct. 15, 1999, the contents of which are fully incorporated herein by reference.

SEQUENCE LISTING

Applicants also enclose a computer readable form of a Sequence Listing.

FIELD OF THE INVENTION

The present invention relates to a method of altering the substrate specificity of a lipolytic enzyme by modifying the amino acid sequence, and to lipolytic enzyme variants obtained by such modification. The invention also relates to a screening method for lipolytic enzymes.

BACKGROUND OF THE INVENTION

Lipolytic enzymes (such as lipases and phospholipases) are capable of hydrolyzing carboxylic ester bonds in a substrate to release carboxylic acids. The hydrolytic activity on different ester bonds is important for the usefulness of the lipolytic enzyme in various industrial applications.

Thus, enzymes with a high phospholipase activity are useful in a wide range of applications such as baking (U.S. Pat. No. 4,567,046), filtration of wheat starch hydrolysate (U.S. Pat. No. 5,264,367) and treatment of vegetable oil to reduce the content of phospholipid (U.S. Pat. No. 5,264,367). For the treatment of vegetable oil, the enzyme should have a low lipase activity, i.e. a low hydrolytic activity towards ester bonds in triglycerides.

WO 98/45453 indicates that an enzyme with a high hydrolytic activity on digalactosyl diglyceride (DGDG) is useful in baking.

It is well known to add a lipase to laundry detergents to aid in the removal of greasy soils (e.g. EP 258,068).

The release of short-chain fatty acids as free fatty acids (FFA) may be desirable for flavor development in food products, e.g. in cheese ripening (M. Hanson, ZFL, 41 (10), 664-666 (1990)).

The three-dimensional (3D) structure of several lipolytic enzymes is known, and several structures are known to contain a so-called "lid" which may be in an open or closed state covering the active site. Brady et al., Nature, 343, 767-770 (1990). Brzozowski A M et al., Nature, 351, 491 (1991). Derewenda et al., Biochemistry, 31 (5), 1532-1541 (1992).

F. Hara et al., JAOCS, 74 (9), 1129-32 (1997) indicates that some lipases have a certain phospholipase activity, whereas most lipases have little or no activity on phospholipids. Thus, phospholipase activity has been described in the lipases from guinea pig pancreas, *Fusarium oxysporum* and *Staphylococcus hyicus*, and attempts have been made to relate the phospholipase activity to the structure of the lipase. WO 98/26057; M. D. van Kampen et al., Chemistry and Physics of Lipids, 93 (1998), 39-45; A. Hjorth et al., Biochemistry 1993, 32, 4702-4707.

The prior art has described the effect on chain-length selectivity by amino acid substitutions in a lipase from *Rhizopus delemar*. Thus, R. D. Joerger et al., Lipids, 29 (6), 377-384 (1994) indicates that the variants F95D, F112W and V209W have an altered preference to $C_4$ and $C_8$ acids. R. R. Klein et al., JAOCS, 74 (11), 1401-1407 (1997) shows that the variant V206T+F95D has a higher selectivity for $C_8$ acid. R. R. Klein et al., Lipids, 32 (2), 123-130 (1997) indicates that the variants V209W+F112W, V94W and F95D+F214R have a higher hydrolytic activity towards $C_4$ and $C_8$ acids, and suggests that structural determinants for medium-chain length specificity may reside in the distal end of the acyl binding groove.

SUMMARY OF THE INVENTION

The inventors have found that the substrate specificity of a lipolytic enzyme can be modified by making alterations to the amino acid sequence in a defined region of the lipolytic enzyme, so as to increase the level of a desired activity or to decrease the level of an undesired activity. Thus, the inventors have developed lipolytic enzymes with a modified amino acid sequence (hereinafter called lipolytic enzyme variants, or variants for short) with a substrate specificity which can be tailored for specific uses.

Accordingly, the invention provides a method of producing a lipolytic enzyme variant and lipolytic enzyme variants prepared by the method. The method comprises:

a) selecting a substrate and an ester bond of interest,
b) selecting a parent lipolytic enzyme,
c) selecting at least one amino acid residue in a region near the active site, near the C-terminal or in the lid region of the parent lipolytic enzyme as described below,
d) making alterations each of which is an insertion, a deletion or a substitution of the amino acid residue,
e) optionally, making alterations each of which is an insertion, a deletion or a substitution of an amino acid residue at one or more positions other than c),
f) preparing the resulting variant,
g) testing the activity of the variant on the ester bond in the substrate, and
h) selecting a variant having an altered activity on the ester bond.

Thus, in one aspect, the parent lipolytic enzyme has an alcohol binding site having a glycerol part with an sn2 position, and the amino acid alteration is within 10 Å of the C atom at the sn2 position of the glycerol part of a substrate triglyceride.

In another aspect, the parent lipolytic enzyme has a structure comprising a catalytic triad consisting of an active Ser, an active Asp and an active His residue, and the amino acid to be altered is either located between the active His residue of the catalytic residue and the C-terminal, or belongs to a set E defined by the following steps:

i) aligning the structure of the lipolytic enzyme with *Rhizomucor miehei* lipase structure 4TGL comprising a catalytic triad and an inhibitor phosphorus atom (4TGL-inhP), so as to minimize the sum of squares of deviation between atoms of the catalytic triads of the two structures, ii) defining a set A consisting of atoms of the lipolytic enzyme inside a sphere of radius 18 Å with center at 4TGL-inhP, iii) forming a first plane defined by 4TGL-inhP, the Cα atom of the active Ser residue of the parent lipolytic enzyme, and the Cα atom of the active Asp residue of the parent lipolytic enzyme and defining a set B as a subset of set A consisting of atoms on the same side of the first plane as the Cα atom of the active His residue of the parent lipolytic enzyme, iv) forming a second plane defined by 4TGL-inhP, the Cα atom of the active Ser residue of the parent lipolytic enzyme, and the Cα atom of the active His residue of the parent lipolytic enzyme and defining a set C as a subset of set A consisting of atoms on the opposite side of the second plane from the Cα atom of the active Asp residue of the parent lipolytic enzyme, v) forming a set D consisting of atoms belonging to the union of sets B and C, and having a solvent accessibility of 15 or higher, and vi) forming set E consisting of amino acid residues in the structure which comprise an atom belonging to set D or an atom belonging to the union of sets B and C and located less than 3.5 Å from an atom belonging to set D, In a third aspect, the lipolytic enzyme has an active site comprising an active His residue, and the alteration is made in the amino acid sequence between the active His residue and the C-terminal.

In yet another aspect of the invention, the amino acid alteration is made among the 10 amino acid residues at the C-terminal.

In a further aspect, the parent lipolytic enzyme has a lid, and the alteration is made in the lid.

The invention also provides a DNA sequence encoding the variant, an expression vector comprising the DNA sequence, a transformed host cell harboring the DNA sequence or the expression vector, and to a method of producing the variant by cultivating the transformed host cell so as to produce the variant and recovering the variant from the resulting broth. Further, the invention provides uses of the variants.

The inventors have also found that a lipolytic enzyme which has lipase and phospholipase activity as well as activity on digalactosyl diglyceride is particularly effective for use in baking, and they designed a screening method for lipolytic enzymes by testing for these activities.

BRIEF DESCRIPTION OF DRAWINGS

FIG. 1 shows an alignment of lipase sequences as follows.
"rhimi" shows the *Rhizomucor miehei* lipase (SEQ ID NO:30)
"rhidl" shows the *Rhizomucor delemar* lipase (SEQ ID NO:31)
"SP400" shows the *Thermomyces (Humicola) lanuginosus* lipase (SEQ ID NO:32)
"Pcl" shows the *Penicillium camemberti* lipase (SEQ ID NO:33)
"FoLnp11" shows the *Fusarium oxysporum* lipase (SEQ ID NO:34)

DETAILED DESCRIPTION OF THE INVENTION

Altered Activity on Selected Ester Bond in Substrate

Compared to the parent lipolytic enzyme, the invention aims to alter the activity on at least one selected ester bond in at least one substrate, i.e. to increase a desired activity, decrease an undesired activity or to change the substrate specificity by decreasing the ratio of an undesired activity to a desired activity.

Thus, an enzyme with increased phospholipase activity may be useful, e.g., in baking or in purification of vegetable oil. It may be desired to increase the hydrolytic activity on digalactosyl-diglyceride (DGDG) for use in baking.

It may be desired to increase the lipase activity for any industrial use where lipases are used. For use in detergents or baking it may be desired to increase the activity on long-chain ($C_{16}$-$C_{20}$) triglycerides, and it may be desired to increase the specificity for long-chain fatty acids by decreasing the ratio of activity on short-chain or medium-chain ($C_4$-$C_8$) fatty acids to the activity on long-chain fatty acids.

For use in, or for use in flavor development in food products (such as cheese ripening) it may be desired to increase the lipase activity on short-chain or medium-chain ($C_4$-$C_8$) triglycerides.

For use as a phospholipase in purification of vegetable oil, it may be desired to decrease the ratio of lipase activity on long-chain ($C_{16}$-$C_{20}$) triglycerides to the phospholipase activity.

Parent Lipolytic Enzyme

The lipolytic enzyme to be used in the present invention is one that can hydrolyze ester bonds. Such enzymes include, for example, lipases, such as triacylglycerol lipase (EC 3.1.1.3), lipoprotein lipase (EC 3.1.1.34), monoglyceride lipase (EC 3.1.1.23), lysophospholipase, ferulic acid esterase and esterase (EC 3.1.1.1, EC 3.1.1.2). The numbers in parentheses are the systematic numbers assigned by the Enzyme Commission of the International Union of Biochemistry in accordance with the type of the enzymatic reactivity of the enzyme.

The parent lipolytic enzyme may be prokaryotic, particularly a bacterial enzyme, e.g. from *Pseudomonas*. Examples are *Pseudomonas* lipases, e.g. from *P. cepacia* (U.S. Pat. No. 5,290,694, pdb file 1OIL), *P. glumae* (N Frenken et al. (1992), Appl. Envir. Microbiol. 58 3787-3791, pdb files 1TAH and 1QGE), *P. pseudoalcaligenes* (EP 334 462) and *Pseudomonas* sp. strain SD 705 (FERM BP-4772) (WO 95/06720, EP 721 981, WO 96/27002, EP 812 910). The *P. glumae* lipase sequence is identical to the amino acid sequence of *Chromobacterium viscosum* (DE 3908131 A1). Other examples are bacterial cutinases, e.g. from *Pseudomonas* such as *P. mendocina* (U.S. Pat. No. 5,389,536) or *P. putida* (WO 88/09367).

Alternatively, the parent lipolytic enzyme may be eukaryotic, e.g. a fungal lipolytic enzyme such as lipolytic enzymes of the Humicola family and the Zygomycetes family and fungal cutinases.

Examples of fungal cutinases are the cutinases of *Fusarium solani pisi* (S. Longhi et al., Journal of Molecular Biology, 268 (4), 779-799 (1997)) and *Humicola insolens* (U.S. Pat. No. 5,827,719).

The Humicola family of lipolytic enzymes consists of the lipase from *H. lanuginosa* strain DSM 4109 and lipases having more than 50% homology with said lipase. The lipase from *H. lanuginosa* (synonym *Thermomyces lanuginosus*) is described in EP 258 068 and EP 305 216, and has the amino acid sequence shown in positions 1-269 of SEQ ID NO: 2 of U.S. Pat. No. 5,869,438.

The Humicola family also includes the following lipolytic enzymes: lipase from *Penicillium camembertii* (P25234), lipase/phospholipase from *Fusarium oxysporum* (EP 130064, WO 98/26057), lipase from *F. heterosporum* (R87979), lysophospholipase from *Aspergillus foetidus* (W33009), phospholipase A1 from *A. oryzae* (JP-A 10-155493), lipase from *A. oryzae* (D85895), lipase/ferulic acid esterase from *A. niger* (Y09330), lipase/ferulic acid esterase from *A. tubingensis* (Y09331), lipase from *A. tubingensis* (WO 98/45453), lysophospholipase from *A. niger* (WO 98/31790), lipase from *F. solanii* having an isoelectric point of 6.9 and an apparent molecular weight of 30 kDa (WO 96/18729).

The Zygomycetes family comprises lipases having at least 50% homology with the lipase of *Rhizomucor miehei* (P19515). This family also includes the lipases from *Absidia reflexa*, *A. sporophora*, *A. corymbifera*, *A. blakesleeana*, *A. griseola* (all described in WO 96/13578 and WO 97/27276) and *Rhizopus oryzae* (P21811). Numbers in parentheses indicate publication or accession to the EMBL, GenBank, GeneSeqp or Swiss-Prot databases.

It is of particular interest to derive a variant with phospholipase activity from a parent lipolytic enzyme having no or very little phospholipase activity, e.g. corresponding to a ratio of phospholipase activity to lipase activity below 0.1 PHLU/LU or below 50 PHLU/mg.

Alteration Near Alcohol Binding Site

As already stated, the amino acid sequence of the parent lipolytic enzyme may be modified at a position which near the glycerol part of a substrate triglyceride. This region will be referred to as the "alcohol binding site" of the lipase; it is described in Brzozowski A M et al., Nature, 351: 491 (1991); Uppenberg et al., Biochemistry, 1995, 34, 16838-16851; A. Svendsen, Inform, 5(5), 619-623 (1994).

For the *Rhizomucor miehei* lipase, the extent of the alcohol binding site can be found from the PDB file "5tgl.pdb" available in Structural Classification of Proteins (SCOP) on the Internet, at rcsb.org/pdb/, showing the complex with the inhibitor n-hexylphosphonate ethyl ester which mimics the substrate. It is described in Derewenda et al. (supra), Brzozowski et al. (supra) and Brady et al. (supra). The sn2 position of this model is the atom CE2.

The variant typically contains no more than 10 alterations in the alcohol binding site, e.g. 1, 2, 3, 4, 5 or 6 alterations.

The alteration may particularly be in that part of the alcohol binding site which comes within 20 positions (e.g. within 10 positions) of the C-terminal.

As already stated, the amino acid sequence of the parent lipolytic enzyme may be modified at a position which is within 10 Å (e.g. within 8 Å, particularly within 6 Å) of the C atom at the sn2 position of the glycerol part of a substrate triglyceride. The following amino acid positions lie within 10 Å of the sn2 position in the *Rhizomucor miehei* lipase: 25, 28, 80-84, 88, 143-146, 175, 203, 205, 254-255, 257-259, 264-267. The following are within 8 Å: 81-83, 144, 257-258, 265-267, and the following within 6 Å: 82, 144, 257, 266.

In the *Humicola lanuginosa* lipase, the following positions are within 10 Å of the sn2 position: 18, 21, 81-85, 89, 145-148, 172, 201, 203, 255-256, 258-260, 264-267. The following are within 8 Å: 82-84, 89, 146, 258-259, 265-267, and the following within 6 Å: 83, 146, 258, 266.

Alteration Near Catalytic Triad

As already stated, in one aspect the parent lipolytic enzyme has a structure comprising a catalytic triad consisting of an active Ser, an active Asp and an active His residue, and the amino acid to be altered belongs to a set defined by a certain procedure described above. The structure may be an open or a closed structure, and it may or may not include a substrate or an inhibitor.

The procedure is conveniently performed by use of software such as MSI's Insight II. It involves alignment with 4TGL, a crystal structure of the lipase from *Rhizomucor miehei* inhibited irreversibly by diethyl p-nitrophenyl phosphate. This is available in Structural Classification of Proteins (SCOP) on the Internet, at rcsb.org/pdb/, and is described in Derewenda et al. (supra).

The *Rhizomucor miehei* lipase comprises a catalytic triad consisting of the amino acid residues S144, D203 and H257.

For the *Humicola lanuginosa* lipase, the structure 1tib may be used; it is available in Structural Classification of Proteins (SCOP) on the Internet. Using this structure, the set defined by the procedure includes the following positions: 10-23, 26, 40, 55-64, 80-87, 116-117, 119, 145-149, 151, 168, 170, 194, 196-201, 220-222, 224-227, and 254-269.

Alteration Between at C-Terminal Side of the Active His Residue

As stated above, one or more alterations may be made in the amino acid sequence between an active His residue and the terminal, specifically among the 12 amino acids at the C-terminal side of the active His.

The *Humicola lanuginosa* lipase has an active His at H258 and the C-terminal at L269, so this region includes positions 259-269. The *P. cepacia* lipase has an active H286 and the C-terminal at residue 297, so the region includes residues 287-297.

Alteration Near C-Terminal

As stated above, one or more alterations may be made within 10 amino acid positions from the C-terminal of the mature protein, or at positions corresponding to such positions in the *H. lanuginosa* lipase, i.e. positions 260-269 of the *H. lanuginosa* lipase. Corresponding positions may be found by alignment of the two sequences as described later in this specification.

The lipolytic enzyme variant may be truncated by deleting amino acid residues corresponding to the first 1, 2, 3, 4, 5 or 6 positions at the C-terminal. A truncated variant may have improved thermostability.

Alternatively, the variant may carry a peptide extension at the C-terminal and/or the N-terminal. The C-terminal extension may consist of 1-10 amino acid residues, e.g. A, P, AG, DG, PG, AGG, PVGF (SEQ ID NO. 15), AGRF (SEQ ID NO. 16), PRGF (SEQ ID NO. 17), AGGF (SEQ ID NO. 18) or AGGFS (SEQ ID NO. 19); or it may consist of 40-50 residues, e.g., consisting of the 48 C-terminal residues of the *Fusarium oxysporum* lipase AGGFSWRRYRSAESVD-KRATMTDAELEKKLNSYVQMDKEYVKNNQARS (SEQ ID NO. 20). The C-terminal extension may increase the phospholipase activity.

Some alterations in the region overlapping with the alcohol binding site are described below.

A specific alteration is a substitution at a position corresponding to G266 in the *Humicola lanuginosa* lipase, specifically with an amino acid of intermediate size, e.g. A, C, D, N, L, I, S, T, P or V. Such alteration alone has been found sufficient to increase the phospholipase activity.

Other specific alterations are such that alter the tertiary structure, e.g. by introducing bulky side chains or by disrupting the bond angles, e.g. by introducing Pro. Such alterations may be made at positions corresponding to positions G263, L264, I265, T267 or L269 in the *Humicola lanuginosa* lipase. Some specific substitutions are G263A,E,Q,R; L264A,C,P, Q; I265L,N,T; T267A,Q or L269N.

Alteration in Lid

As stated above, the amino acid sequence of the prent lipolytic enzyme may be modified in the lid region of the parent lipolytic enzyme. This region is described in Brady et al., *Nature* 343, 1990, pp. 767-770 and in Brzozowski A M et al., *Nature*, 351: 491 (1991). In the *H. lanuginosa* lipase, the lid is located at positions 80-100, and the modification may particularly be made at positions 82-98, e.g. 91-98.

The variant typically contains no more than 5 alterations in the lid region; it may contain 0, 1, 2 or 3 alterations. A specific alteration is a substitution of an amino acid corresponding to G91, L93, N94, D96, K98, L97 and/or E99 in the *Humicola lanuginosa* lipase with a neutral or positively charged amino acid, e.g. a substitution corresponding to G91A,T, L93K, N94D, D96S,W,G, L97Q, K98D,F,E and/or E99K,D.

Specifically, a variant with an alteration in the lid region also contains one or more alterations near the catalytic triad, near the substrate binding site or near the C-terminal.

Lipolytic Enzyme Variants

The lipolytic enzyme variant of the invention comprises one or more alterations of an amino acid residue in any of the regions described above. Each alteration may be a deletion or a substitution of the amino acid residue, or it may be an insertion before or after the amino acid residue. If the amino acid residue is at the C-terminal, the insertion may be a C-terminal extension. An insertion typically consists of 1-5 amino acid residues, e.g. 1-2, and a C-terminal extension may consist of 1-50 or 2-10 amino acid residues.

The total number of alterations in the above regions is typically not more than 20, e.g. not more than 10 or not more than 5, and there may be as little as 1 or 2 alterations in the above regions.

In addition, the lipolytic enzyme variant of the invention may optionally include other modifications of the parent enzyme, typically not more than 10, e.g. not more than 5 such modifications.

The variant generally has a homology with the parent lipolytic enzyme of at least 80%, e.g. at least 85%, typically at least 90% or at least 95%.

The variant of the invention may further comprise a peptide extension at the N-terminal, e.g. consisting of 1-15 (particularly 4-10) amino acid residues, and specifically comprising 1, 2 or 3 positively charged amino acids. Some specific N-terminal peptide extensions are AS, SPIRR (SEQ ID NO. 21), E1RP, E1SPIRPRP (SEQ ID NO. 22), E1SPPRRP (SEQ ID NO. 23) and E1SPIRPRP (SEQ ID NO. 22). Further, any peptide extension described in WO 97/04079 and WO 97/07202 may be used.

Specific Variants

To prepare variants of a lipolytic enzyme of the Humicola family, the amino acid alterations may specifically be made at positions corresponding to 20-25, 56-64, 81-85 or 255-269 in the *Humicola lanuginosa* lipase. Thus, the alteration may be a substitution, deletion or insertion at a position corresponding to A20, Y21, G23, K24, N25, V63, R81, G82, R84, A257, W260, Y261, F262 or G266 (e.g. excluding G23C, K24C, R81C), a substitution of an amino acid corresponding to C268 or L269.

Some specific alterations are substitutions corresponding to the following in *H. lanuginosa* lipase: Y21V/I/L/A/G/M/M/W/P/F/N/Q/S/T, V60V/I/L/A/G/M/W/P/F/N/Q/S/T, G61V/I/L/A/G/M/W/P/F/N/Q/S/T, D62E/A/V, S83T, R84K/L/W, P256A, G263E,Q,R,F, L264A,C,P,F,G,I, I265L,N,F G266D/E or T267A,Q,P,S,E, or an insertion corresponding to T267GS or T267GL.

To alter the activity towards short-chain ($C_4$-$C_8$) fatty acids in triglycerides, alterations may be made at positions corresponding to Y21, E56, D57, V60, G61, D62, R81, S83, R84, L259, Y261 or G266, e.g. a substitution corresponding to Y21V/I, V60G, D62E/A/V, S83T, R84K/L/W or G266D/E.

To increase the activity for DGDG, alterations may be made at positions corresponding to Y21, G23, N26, D57, D62, R81, S83, R84, S85, G266, T267 or L269; e.g., two or more such alterations may be made, e.g. together with one or more alterations in the lid region. To increase the phospholipase activity, alterations may be made at positions corresponding to R81, R84, S85, or 263-267, e.g. G266 or T267.

To prepare variants of a *Pseudomonas lipase*, amino acid modifications may be made at positions corresponding to 12-13, 16-34, 45-52, 59-66, 68, 86-87, 107-109, 111, 143-153, 155, 157-158, 207-212, 228, 230, 242-249, 264, 279-280, 282-297, 301-302, 304-305, 307-308 in the *P. cepacia* lipase, particularly L17/L17, T18/A18, Y29/Y29, L287/L286, E289/E288, I290/I289, Q292/Q291 or L293/L292 in the *P. cepacia/P. glumae* lipase.

Specific variants of the *H. lanuginosa* lipase are disclosed in the examples. Corresponding alterations may be made in other parent lipolytic enzymes. Further variants may be derived from these by omitting amino acid modifications at positions 1, 106, 186, 225, 232, 237, 239 or 274. Variants with 274S may optionally have a further C-terminal extension of WRRyRSAESVDKRATMTDAELEKKLN-SYVQMDKEYVKNNQARS (SEQ ID NO. 24) (corresponding to the C-terminal of the *F. oxysporum* lipase) in full or truncated form.

Nomenclature for Amino Acid Alterations

The nomenclature used herein for defining mutations is basically as described in WO 92/05249. Thus, G91A indicates substitution of G in position 91 with A. T267A,Q indicates substitution of T at position 267 with A or Q. E1E,D,A indicates that E1 is unchanged or is substituted with D or A.

T267stop indicates a stop codon, i.e. deletion of T267 and all following amino acids (i.e. C268 and L269). 270P, 271V indicates a C-terminal extension of PV (i.e. at new positions 270 and 271). –G266 indicates deletion of G at position 266. Parentheses indicate that the alteration is optional, or in examples that the alteration is uncertain. SPIRR (SEQ ID NO. 21) indicates an N-terminal extension. D266 may refer to the position or to substitution with any amino acid (except D).

E1SPPCGRRP (SEQ ID NO. 25) or SPPCGRRP(-E) (SEQ ID NO. 25) indicates a substitution of E1 with SPPCGRRP (SEQ ID NO. 25), i.e. a peptide addition at the N-terminal. T267GS indicates a substitution of T267 with GS, or in other words the substitution T267G and an insertion of S between G267 and C268.

Homology and Alignment

For purposes of the present invention, the degree of homology may be suitably determined by means of computer programs known in the art, such as GAP provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45), using GAP with the following settings for polypeptide sequence comparison: GAP creation penalty of 3.0 and GAP extension penalty of 0.1.

In the present invention, corresponding (or homologous) positions in the lipase sequences of *Rhizomucor miehei* (rhimi), *Rhizopus delemar* (rhidl), *Thermomyces lanuginosa* (former; *Humicola lanuginosa*) (SP400), *Penicillium camembertii* (Pcl) and *Fusarium oxysporum* (FoLnp11), are defined by the alignment shown in FIG. 1.

To find the homologous positions in lipase sequences not shown in the alignment, the sequence of interest is aligned to the sequences shown in FIG. 1. The new sequence is aligned to the present alignment in FIG. 1 by using the GAP alignment to the most homologous sequence found by the GAP program. GAP is provided in the GCG program package (Program Manual for the Wisconsin Package, Version 8, August 1994, Genetics Computer Group, 575 Science Drive, Madison, Wis., USA 53711) (Needleman, S. B. and Wunsch, C. D., (1970), Journal of Molecular Biology, 48, 443-45). The following settings are used for polypeptide sequence comparison: GAP creation penalty of 3.0 and GAP extension penalty of 0.1.

Variants with Phospholipase Activity

As described above, the variant of the invention may have a higher phospholipase activity than the parent lipolytic enzyme. By the monolayer method described later in this specification, the variant may have a phospholipase activity of at least 0.1 nmol/min at pH 5.

By the PHLU method described later in this specification, the variant may have a phospholipase activity of at least 100 PHLU/mg (mg of pure enzyme protein), particularly at least 500 PHLU/mg. The variant has a ratio of phospholipase activity to lipase activity (both measured at pH 7) of at least 0.1 PHLU/LU, e.g. at least 0.5, particularly at least 2.

The variants of the invention may have the ability to hydrolyze intact phospholipid, as demonstrated by the PHLU method. They may have $A_1$ and/or $A_2$ activity, so they may be able to hydrolyze one or both fatty acyl groups in the phospholipid.

pH Optimum

Many variants of the *Humicola lanuginosa* lipase have an alkaline pH optimum for lipase activity and an acid pH optimum for phospholipase activity (e.g. pH 9-10 for lipase and pH 4-6 for phospholipase). Such variants can be used at acid pH (e.g. in oil degumming, described later), as phospholipases with very low concomitant lipase activity.

However, some variants of the *Humicola lanuginosa* lipase which include the substitution G266D,E have pH optima for both lipase and phospholipase activities around pH 5-6. Such variants may be used at acid pH when both lipase and phospholipase activities are desired, e.g. in baking.

Thermostability

The thermostability of the variant can conveniently be evaluated by means of Differential Scanning Calorimetry (DSC). Depending on exact mutations, the variants of the invention generally have similar or slightly lower thermostability than the parent lipolytic enzyme.

The temperature at the top of the denaturation peak ($T_d$) of the lipase from *Humicola lanuginosa* when heated at 90 deg/hr at pH 5 is just above 70° C. (=$T_d$). $T_d$ for the variants of the invention is generally 5-10 degrees lower Use of Variant Depending on the substrate specificity, variants of the invention can be used, e.g., in filtration improvement, vegetable oil treatment, baking, detergents, or preparation of lysophospholipid.

Improvement of Filtration

A variant with lysophospholipase activity can be used to improve the filterability of an aqueous solution or slurry of carbohydrate origin by treating it with the variant. This is particularly applicable to a solution or slurry containing a starch hydrolysate, especially a wheat starch hydrolysate since this tends to be difficult to filter and to give cloudy filtrates. The treatment can be done in analogy with EP 219, 269 (CPC International).

Vegetable Oil Treatment

A variant with phospholipase activity can be used in a process for reducing the content of phospholipid in an edible oil, comprising treating the oil with the variant so as to hydrolyze a major part of the phospholipid, and separating an aqueous phase containing the hydrolyzed phospholipid from the oil. This process is applicable to the purification of any edible oil which contains phospholipid, e.g. vegetable oil such as soy bean oil, rape seed oil and sunflower oil. The treatment may be carried out at acid pH, e.g. pH 3-5. Advantageously, a variant can be selected so as to have a high phospholipase activity and a low lipase activity at low pH, due to different pH optima of the two activities.

The process for oil treatment can be conducted according to principles known in the art, e.g. in analogy with U.S. Pat. No. 5,264,367 (Metallgesellschaft, Röhm); K. Dahlke & H. Buchold, INFORM, 6 (12), 1284-91 (1995); H. Buchold, Fat Sci. Technol., 95 (8), 300-304 (1993); JP-A 2-153997 (Showa Sangyo); or EP 654,527 (Metallgesellschaft, Röhm).

Miscellaneous Uses of Phospholipase

A variant with phospholipase activity can be used to prepare lysophospholipid (e.g. lyso-lecithin) by treating the corresponding phospholipid with the variant, e.g. as described in EP 870840, JP-A 10-42884, JP-A 4-135456 or JP-A 2-49593. The variant can also be used to make mayonnaise, e.g. as described in EP 628256, EP 398666 or EP 319064.

A variant with phospholipase activity may also be used in the processing of dairy and other food products, e.g. as described in EP 567,662 (Nestlé), EP 426,211 (Unilever), EP 166,284 (Nestlé), JP-A 57-189638 (Yakult) or U.S. Pat. No. 4,119,564 (Unilever).

The variant may be used leather treatment, as described in JP-A 7-177884 (Kao).

Baking

A variant with phospholipase and/or DGDGase activity can be used in the preparation of dough, bread and cakes, e.g. to increase dough stability and dough handling properties, or to improve the elasticity of the bread or cake. Thus, the variant can be used in a process for making bread, comprising adding the variant to the ingredients of a dough, kneading the dough and baking the dough to make the bread. This can be done in analogy with U.S. Pat. No. 4,567,046 (Kyowa Hakko), JP-A 60-78529 (QP Corp.), JP-A 62-111629 (QP Corp.), JP-A 63-258528 (QP Corp.), EP 426211 (Unilever) or WO 99/53769 (Novo Nordisk).

It is particularly advantageous to use the variant together with an anti-staling endo-amylase and optionally also to add a phospholipid, to reduce-staling of the bread and particularly to improve softness of the bread in the first 24 hours after baking. The endo-amylase may be a maltogenic α-amylase (e.g. from *Bacillus* sp., such as Novamyl® from Novo Nordisk) or a fungal or bacterial α-amylase, e.g. from *Aspergillus* or *Bacillus*, particularly *A. oryzae, B. licheniformis* or *B. amyloliquefaciens*.

In baking, the variant may have a low activity on short-chain or medium-chain ($C_4$-$C_8$), e.g. corresponding to a SLU/LU ratio above 3. The use of such a variant may avoid or suppress the development of an undesired flavor due to the release of short-chain fatty acids. The variant may have activity on triglycerides and phospholipid as well as DGDG.

Cheese Flavor

A variant with activity towards short-chain fatty acyl groups may be used to release free fatty acids (FFA) for flavor development in food products, e.g. in cheese ripening, e.g. as described in M. Hanson, ZFL, 41 (10), 664-666 (1990)).

Lipolytic enzyme variants with increased release of short chain fatty compared to long chain fatty acids from milk fat are useful in cheese production, e.g. for flavor enhancement or shortening of the ripening times for ripened cheeses, like cheddar or parmesan. Another application for such lipolytic enzyme variants is for enzyme modified cheese (EMC) for use as flavoring for various food products including process cheese, dressing and snack.

Release of short chain fatty acids, like butyric acid, is essential for the development of cheese flavor, whereas release of long chain fatty acids, like oleic acid, give rise to off flavors. Lipolytic enzyme variants for cheese applications, including EMC, should have SLU/LU ratio of less than 0.5, e.g. less than 0.25, most preferable less than 0.1

Use in Detergent

The variant may be used as a detergent additive, e.g. at a concentration (expressed as pure enzyme protein) of 0.001-10 (e.g. 0.01-1) mg per gram of detergent or 0.001-100 (e.g. 0.01-10) mg per liter of wash liquor.

In detergents, the variant may have a high activity on long-chain triglycerides ($C_{16}$-$C_{20}$) to improve the removal of fatty soiling. The variant may have phospholipase activity. The variant may have low activity towards short-chain ($C_4$-$C_8$) fatty acids in triglycerides, e.g. corresponding to a SLU/LU ratio above 10. The use of such a variant may avoid or suppress the development of an undesired odor due to the release of short-chain fatty acids.

Variants having both lipase and phospholipase activity at alkaline pH may be used in detergents.

Detergent Composition

The detergent composition of the invention may for example be formulated as a hand or machine laundry detergent composition including a laundry additive composition suitable for pre-treatment of stained fabrics and a rinse added fabric softener composition, or be formulated as a detergent composition for use in general household hard surface cleaning operations. In a laundry detergent, the variant may be effective for the removal of fatty stains, for whiteness maintenance and for dingy cleanup. A laundry detergent composition may be formulated as described in WO 97/04079, WO 97/07202, WO 97/41212, PCT/DK WO 98/08939 and WO 97/43375.

The detergent composition of the invention may particularly be formulated for hand or machine dishwashing operations. e.g. as described in GB 2,247,025 (Unilever) or WO 99/01531 (Procter & Gamble). In a dishwashing composition, the variant may be effective for removal of greasy/oily stains, for prevention of the staining/discoloration of the dishware and plastic components of the dishwasher by highly colored components and the avoidance of lime soap deposits on the dishware.

The detergent composition of the invention may be in any convenient form, e.g., a bar, a tablet, a powder, a granule, a paste or a liquid. A liquid detergent may be aqueous, typically containing up to 70% water and 0-30% organic solvent, or non-aqueous.

The detergent composition comprises one or more surfactants, which may be non-ionic including semi-polar and/or anionic and/or cationic and/or zwitterionic. The surfactants are typically present at a level of from 0.1% to 60% by weight, e.g. 0.5-40%, such as 1-30%, typically 1.5-20%.

When included therein the detergent will usually contain from about 1% to about 40% of an anionic surfactant such as linear alkylbenzenesulfonate, alpha-olefinsulfonate, alkyl sulfate (fatty alcohol sulfate), alcohol ethoxysulfate, secondary alkanesulfonate, alpha-sulfo fatty acid methyl ester, alkyl- or alkenylsuccinic acid or soap.

When included therein the detergent will usually contain from about 0.2% to about 40% of a non-ionic surfactant such as alcohol ethoxylate, nonyl-phenol ethoxylate, alkylpolyglycoside, alkyldimethylamine-oxide, ethoxylated fatty acid monoethanol-amide, fatty acid monoethanolamide, polyhydroxy alkyl fatty acid amide, or N-acyl N-alkyl derivatives of glucosamine ("glucamides").

The invention also provides a detergent additive comprising the variant of the invention. The detergent additive as well as the detergent composition may comprise one or more other enzymes such as a protease, a lipase, a cutinase, an amylase, a carbohydrase, a cellulase, a pectinase, a mannanase, an arabinase, a galactanase, a xylanase, an oxidase, e.g., a laccase, and/or a peroxidase.

In general the properties of the chosen enzyme(s) should be compatible with the selected detergent, (i.e. pH-optimum, compatibility with other enzymatic and non-enzymatic ingredients, etc.), and the enzyme(s) should be present in effective amounts.

Proteases: Suitable proteases include those of animal, vegetable or microbial origin. Microbial origin is preferred. Chemically modified or protein engineered mutants are included. The protease may be a serine protease or a metallo protease, e.g. an alkaline microbial protease or a trypsin-like protease. Examples of alkaline proteases are subtilisins, especially those derived from *Bacillus*, e.g., subtilisin Novo, subtilisin Carlsberg, subtilisin 309, subtilisin 147 and subtilisin 168 (described in WO 89/06279). Examples of trypsin-like proteases are trypsin (e.g. of porcine or bovine origin) and the *Fusarium* protease described in WO 89/06270 and WO 94/25583.

Examples of useful proteases are the variants described in WO 92/19729, WO 98/20115, WO 98/20116, and WO 98/34946, especially the variants with substitutions in one or more of the following positions: 27, 36, 57, 76, 87, 97, 101, 104, 120, 123, 167, 170, 194, 206, 218, 222, 224, 235 and 274.

Specific commercially available protease enzymes include ALCALASE®, SAVINASE®, PRIMASE®, DURALASE®, ESPERASE®, and KANNASE® (Novozymes A/S), MAXATASE®, MAXACAL®, MAXAPEM®, PROPERASE®, PURAFECT®, PURAFECT OxP®, FN2™, and FN3™ (Genencor International Inc.).

Cellulases: Suitable cellulases include those of bacterial or fungal origin. Chemically modified or protein engineered mutants are included. Suitable cellulases include cellulases from the genera *Bacillus*, *Pseudomonas*, *Humicola*, *Fusarium*, *Thielavia*, *Acremonium*, e.g. the fungal cellulases produced from *Humicola insolens*, *Myceliophthora thermophila* and *Fusarium oxysporum* disclosed in U.S. Pat. No. 4,435,307, U.S. Pat. No. 5,648,263, U.S. Pat. No. 5,691,178, U.S. Pat. No. 5,776,757 and WO 89/09259.

Especially suitable cellulases are the alkaline or neutral cellulases having colour care benefits. Examples of such cellulases are cellulases described in EP 0 495 257, EP 0 531 372, WO 96/11262, WO 96/29397, WO 98/08940. Other examples are cellulase variants such as those described in WO 94/07998, EP 0 531 315, U.S. Pat. No. 5,457,046, U.S. Pat. No. 5,686,593, U.S. Pat. No. 5,763,254, WO 95/24471, WO 98/12307 and PCT/DK98/00299.

Commercially available cellulases include CELLUZYME®, and CAREZYME®(Novozymes A/S), CLAZINASE®, and PURADAX HA® (Genencor International Inc.), and KAC-500(B)® (Kao Corporation).

Peroxidases/Oxidases: Suitable per-oxidases/oxidases include those of plant, bacterial or fungal origin. Chemically modified or protein engineered mutants are included. Examples of useful peroxidases include peroxidases from *Coprinus*, e.g. from *C. cinereus*, and variants thereof as those described in WO 93/24618, WO 95/10602, and WO 98/15257.

Commercially available peroxidases include Guardzyme® (Novo Nordisk A/S).

The detergent enzyme(s) may be included in a detergent composition by adding separate additives containing one or more enzymes, or by adding a combined additive comprising all of these enzymes. A detergent additive of the invention, i.e. a separate additive or a combined additive, can be formulated e.g. as a granulate, a liquid, a slurry, etc. Specific detergent additive formulations are granulates, in particular non-dusting granulates, liquids, in particular stabilized liquids, or slurries.

Non-dusting granulates may be produced, e.g., as disclosed in U.S. Pat. Nos. 4,106,991 and 4,661,452 and may optionally be coated by methods known in the art. Examples of waxy coating materials are poly(ethylene oxide) products (polyethyleneglycol, PEG) with mean molar weights of 1000 to 20000; ethoxylated nonyl-phenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for in-stance, be stabilized by adding a polyol such as propylene glycol, a sugar or sugar alcohol, lactic acid or boric acid according to established methods. Protected enzymes may be prepared according to the method disclosed in EP 238,216.

The detergent may contain 0-65% of a detergent builder or complexing agent such as zeolite, diphosphate, tripho-sphate, phosphonate, carbonate, citrate, nitrilotriacetic acid, ethylenediaminetetraacetic acid, diethylenetri-aminepen-taacetic acid, alkyl- or alkenylsuccinic acid, soluble silicates or layered silicates (e.g. SKS-6 from Hoechst).

The detergent may comprise one or more polymers. Examples are carboxymethylcellulose, poly(vinyl-pyrrolidone), poly(ethylene glycol), poly(vinyl alcohol), poly(vinylpyridine-N-oxide), poly(vinylimidazole), polycarboxylates such as polyacrylates, maleic/acrylic acid copolymers and lauryl methacrylate/acrylic acid co-polymers.

The detergent may contain a bleaching system which may comprise a H2O2 source such as perborate or percarbonate which may be combined with a peracid-forming bleach activator such as tetraacetylethylenediamine or nonanoyloxyben-zenesul-fonate. Alternatively, the bleaching system may comprise peroxyacids of e.g. the amide, imide, or sulfone type.

The enzyme(s) of the detergent composition of the invention may be stabilized using conventional stabilizing agents, e.g., a polyol such as propylene glycol or glycerol, a sugar or sugar alcohol, lactic acid, boric acid, or a boric acid derivative, e.g., an aromatic borate ester, or a phenyl boronic acid derivative such as 4-formylphenyl boronic acid, and the composition may be formulated as described in e.g. WO 92/19709 and WO 92/19708.

The detergent may also contain other conventional detergent ingredients such as e.g. fabric conditioners including clays, foam boosters, suds suppressors, anti-corrosion agents, soil-suspending agents, anti-soil redeposition agents, dyes, bactericides, optical brighteners, hydrotropes, tarnish inhibitors, or perfumes.

It is at present contemplated that in the detergent compositions any enzyme, in particular the variant of the invention, may be added in an amount corresponding to 0.01-100 mg of enzyme protein per liter of wash liquor, e.g. 0.05-5 mg of enzyme protein per liter of wash liquor, in particular 0.1-1 mg of enzyme protein per liter of wash liquor.

The variant of the invention may additionally be incorporated in the detergent formulations disclosed in WO 97/07202 which is hereby incorporated as reference.

Methods for Preparing Enzyme Variants

The enzyme variant of the invention can be prepared by methods known in the art, e.g. as described in WO 97/04079 (Novo Nordisk). The following describes methods for the cloning of enzyme-encoding DNA sequences, followed by methods for generating mutations at specific sites within the enzyme-encoding sequence.

Cloning a DNA Sequence Encoding a Enzyme

The DNA sequence encoding a parent enzyme may be isolated from any cell or microorganism producing the enzyme in question, using various methods well known in the art. First, a genomic DNA and/or cDNA library should be constructed using chromosomal DNA or messenger RNA from the organism that produces the enzyme to be studied. Then, if the amino acid sequence of the enzyme is known, labeled oligonucleotide probes may be synthesized and used to identify enzyme-encoding clones from a genomic library prepared from the organism in question. Alternatively, a labeled oligonucleotide probe containing sequences homologous to another known enzyme gene could be used as a probe to identify enzyme-encoding clones, using hybridization and washing conditions of lower stringency.

Yet another method for identifying enzyme-encoding clones would involve inserting fragments of genomic DNA into an expression vector, such as a plasmid, transforming enzyme-negative bacteria with the resulting genomic DNA library, and then plating the transformed bacteria onto agar containing a substrate for enzyme (i.e. maltose), thereby allowing clones expressing the enzyme to be identified.

Alternatively, the DNA sequence encoding the enzyme may be prepared synthetically by established standard methods, e.g. the phosphoroamidite method described S. L. Beaucage and M. H. Caruthers, (1981), Tetrahedron Letters 22, p. 1859-1869, or the method described by Matthes et al., (1984), EMBO J. 3, p. 801-805. In the phosphoroamidite method, oligonucleotides are synthesized, e.g. in an automatic DNA synthesizer, purified, annealed, ligated and cloned in appropriate vectors.

Finally, the DNA sequence may be of mixed genomic and synthetic origin, mixed synthetic and cDNA origin or mixed genomic and cDNA origin, prepared by ligating fragments of synthetic, genomic or cDNA origin (as appropriate, the fragments corresponding to various parts of the entire DNA sequence), in accordance with standard techniques. The DNA sequence may also be prepared by polymerase chain reaction (PCR) using specific primers, for instance as described in U.S. Pat. No. 4,683,202 or R. K. Saiki et al., (1988), Science 239, 1988, pp. 487-491.

Site-Directed Mutagenesis

Once a enzyme-encoding DNA sequence has been isolated, and desirable sites for mutation identified, mutations may be introduced using synthetic oligonucleotides. These oligonucleotides contain nucleotide sequences flanking the desired mutation sites. In a specific method, a single-stranded gap of DNA, the enzyme-encoding sequence, is created in a vector carrying the enzyme gene. Then the synthetic nucleotide, bearing the desired mutation, is annealed to a homologous portion of the single-stranded DNA. The remaining gap is then filled in with DNA polymerase I (Klenow fragment) and the construct is ligated using T4 ligase. A specific example of this method is described in Morinaga et al., (1984), Biotechnology 2, p. 646-639. U.S. Pat. No. 4,760,025 discloses the introduction of oligonucleotides encoding multiple mutations by performing minor alterations of the cassette. However, an even greater variety of mutations can be introduced at any one time by the Morinaga method, because a multitude of oligonucleotides, of various lengths, can be introduced.

Another method for introducing mutations into enzyme-encoding DNA sequences is described in Nelson and Long, (1989), Analytical Biochemistry 180, p. 147-151. It involves the 3-step generation of a PCR fragment containing the desired mutation introduced by using a chemically synthesized DNA strand as one of the primers in the PCR reactions. From the PCR-generated fragment, a DNA fragment carrying the mutation may be isolated by cleavage with restriction endonucleases and reinserted into an expression plasmid.

Further, Sierks. et al., (1989) "Site-directed mutagenesis at the active site Trp120 of *Aspergillus awamori* glucoamylase". Protein Eng., 2, 621-625; Sierks et al., (1990), "Catalytic mechanism of fungal glucoamylase as defined by mutagenesis of Asp176, Glu179 and Glu180 in the enzyme from *Aspergillus awamori*". Protein Eng. vol. 3, 193-198; also describes site-directed mutagenesis in an *Aspergillus* glucoamylase.

Expression of Enzyme Variants

According to the invention, a DNA sequence encoding the variant produced by methods described above, or by any alternative methods known in the art, can be expressed, in enzyme form, using an expression vector which typically includes control sequences encoding a promoter, operator, ribosome binding site, translation initiation signal, and, optionally, a repressor gene or various activator genes.

Expression Vector

The recombinant expression vector carrying the DNA sequence encoding a enzyme variant of the invention may be any vector which may conveniently be subjected to recombinant DNA procedures, and the choice of vector will often depend on the host cell into which it is to be introduced. The vector may be one which, when introduced into a host cell, is integrated into the host cell genome and replicated together with the chromosome(s) into which it has been integrated. Examples of suitable expression vectors include pMT838.

Promoter

In the vector, the DNA sequence should be operably connected to a suitable promoter sequence. The promoter may be any DNA sequence which shows transcriptional activity in the host cell of choice and may be derived from genes encoding proteins either homologous or heterologous to the host cell.

Examples of suitable promoters for directing the transcription of the DNA sequence encoding a enzyme variant of the invention, especially in a bacterial host, are the promoter of the lac operon of *E. coli*, the *Streptomyces coelicolor* agarase gene dagA promoters, the promoters of the *Bacillus licheniformis* α-amylase gene (amyL), the promoters of the *Bacillus stearothermophilus* maltogenic amylase gene (amyM), the promoters of the *Bacillus amyloliquefaciens* α-amylase (amyQ), the promoters of the *Bacillus subtilis* xylA and xylB genes etc. For transcription in a fungal host, examples of useful promoters are those derived from the gene encoding *A. oryzae* TAKA amylase, the TPI (triose phosphate isomerase) promoter from *S. cerevisiae* (Alber et al. (1982), J. Mol. Appl. Genet 1, p. 419-434, *Rhizomucor miehei* aspartic proteinase, *A. niger* neutral α-amylase, *A. niger* acid stable α-amylase, *A. niger* glucoamylase, *Rhizomucor miehei* lipase, *A. oryzae* alkaline protease, *A. oryzae* triose phosphate isomerase or *A. nidulans* acetamidase.

Expression Vector

The expression vector of the invention may also comprise a suitable transcription terminator and, in eukaryotes, polyadenylation sequences operably connected to the DNA sequence encoding the α-amylase variant of the invention. Termination and polyadenylation sequences may suitably be derived from the same sources as the promoter.

The vector may further comprise a DNA sequence enabling the vector to replicate in the host cell in question. Examples of such sequences are the origins of replication of plasmids pUC19, pACYC177, pUB110, pE194, pAMB1 and pIJ702.

The vector may also comprise a selectable marker, e.g. a gene the product of which complements a defect in the host cell, such as the dal genes from *B. subtilis* or *B. licheniformis*, or one which confers antibiotic resistance such as ampicillin, kanamycin, chloramphenicol or tetracyclin resistance. Furthermore, the vector may comprise *Aspergillus* selection markers such as amdS, argB, niaD and sC, a marker giving rise to hygromycin resistance, or the selection may be accomplished by co-transformation, e.g. as described in WO 91/17243.

The procedures used to ligate the DNA construct of the invention encoding a enzyme variant, the promoter, terminator and other elements, respectively, and to insert them into suitable vectors containing the information necessary for replication, are well known to persons skilled in the art (cf., for instance, Sambrook et al., Molecular Cloning: A Laboratory Manual, 2nd Ed., Cold Spring Harbor, 1989).

Host Cells

The cell of the invention, either comprising a DNA construct or an expression vector of the invention as defined above, is advantageously used as a host cell in the recombinant production of a enzyme variant of the invention. The cell may be transformed with the DNA construct of the invention encoding the variant, conveniently by integrating the DNA construct (in one or more copies) in the host chromosome. This integration is generally considered to be an advantage as the DNA sequence is more likely to be stably maintained in the cell. Integration of the DNA constructs into the host chromosome may be performed according to conventional methods, e.g. by homologous or heterologous recombination. Alternatively, the cell may be transformed with an expression vector as described above in connection with the different types of host cells.

The cell of the invention may be a cell of a higher organism such as a mammal or an insect, but may be a microbial cell, e.g. a bacterial or a fungal (including yeast) cell.

Examples of suitable bacteria are Gram positive bacteria such as *Bacillus subtilis, Bacillus licheniformis, Bacillus lentus, Bacillus brevis, Bacillus stearothermophilus, Bacillus alkalophilus, Bacillus amyloliquefaciens, Bacillus coagulans, Bacillus circulans, Bacillus lautus, Bacillus megaterium, Bacillus thuringiensis*, or *Streptomyces lividans* or *Streptomyces murinus*, or gramnegative bacteria such as *E. coli*. The transformation of the bacteria may, for instance, be effected by protoplast transformation or by using competent cells in a manner known per se.

The yeast organism may favorably be selected from a species of *Saccharomyces* or *Schizosaccharomyces*, e.g. *Saccharomyces cerevisiae*.

The host cell may also be a filamentous fungus e.g. a strain belonging to a species of *Aspergillus*, such as *Aspergillus oryzae* or *Aspergillus niger*, or a strain of *Fusarium*, such as a strain of *Fusarium oxysporium, Fusarium graminearum* (in the perfect state named *Gribberella zeae*, previously *Sphaeria zeae*, synonym with *Gibberella roseum* and *Gibberella roseum* f. sp. *cerealis*), or *Fusarium sulphureum* (in the prefect state named *Gibberella puricaris*, synonym with *Fusarium trichothecioides, Fusarium bactridioides, Fusarium sambucium, Fusarium roseum*, and *Fusarium roseum* var. *graminearum*), *Fusarium cerealis* (synonym with *Fusarium crokkwellnse*), or *Fusarium venenatum*.

In a specific embodiment of the invention the host cell is a protease deficient of protease minus strain.

This may for instance be the protease deficient strain *Aspergillus oryzae* JaL 125 having the alkaline protease gene named "alp" deleted. This strain is described in WO 97/35956 (Novo Nordisk).

Filamentous fungi cells may be transformed by a process involving protoplast formation and transformation of the protoplasts followed by regeneration of the cell wall in a manner known per se. The use of *Aspergillus* as a host micro-organism is described in EP 238 023 (Novo Nordisk A/S), the contents of which are hereby incorporated by reference.

Method of Producing the Enzyme Variant of the Invention

The enzyme variant of the invention may be produced by a method comprising cultivating a host cell under conditions conducive to the production of the variant and recovering the variant from the cells and/or culture medium.

The medium used to cultivate the cells may be any conventional medium suitable for growing the host cell in question and obtaining expression of the enzyme variant of the invention. Suitable media are available from commercial suppliers or may be prepared according to published recipes (e.g. as described in catalogues of the American Type Culture Collection).

The enzyme variant secreted from the host cells may conveniently be recovered from the culture medium by well-known procedures, including separating the cells from the medium by centrifugation or filtration, and precipitating proteinaceous components of the medium by means of a salt such as ammonium sulphate, followed by the use of chromatographic procedures such as ion exchange chromatography, affinity chromatography, or the like.

Expression of Variant in Plants

The present invention also relates to a transgenic plant, plant part or plant cell which has been transformed with a DNA sequence encoding the variant of the invention so as to express and produce this enzyme in recoverable quantities. The enzyme may be recovered from the plant or plant part. Alternatively, the plant or plant part containing the recombinant enzyme may be used as such.

The transgenic plant can be dicotyledonous or monocotyledonous, for short a dicot or a monocot. Examples of monocot plants are grasses, such as meadow grass (blue grass, *Poa*), forage grass such as festuca, lolium, temperate grass, such as *Agrostis*, and cereals, e.g. wheat, oats, rye, barley, rice, sorghum and maize (corn).

Examples of dicot plants are tobacco, legumes, such as lupins, potato, sugar beet, pea, bean and soybean, and cruciferous (family Brassicaceae), such as cauliflower, oil seed rape and the closely related model organism *Arabidopsis thaliana*.

Examples of plant parts are stem, callus, leaves, root, fruits, seeds, and tubers. In the present context, also specific plant tissues, such as chloroplast, apoplast, mitochondria, vacuole, peroxisomes and cytoplasm are considered to be a plant part. Furthermore, any plant cell, whatever the tissue origin, is considered to be a plant part.

Also included within the scope of the invention are the progeny of such plants, plant parts and plant cells.

The transgenic plant or plant cell expressing the variant of the invention may be constructed in accordance with methods known in the art. In short the plant or plant cell is constructed by incorporating one or more expression constructs encoding the variant of the invention into the plant host genome and propagating the resulting modified plant or plant cell into a transgenic plant or plant cell.

Conveniently, the expression construct is a DNA construct which comprises a gene encoding the variant of the invention in operable association with appropriate regulatory sequences required for expression of the gene in the plant or plant part of choice. Furthermore, the expression construct may comprise a selectable marker useful for identifying host cells into which the expression construct has been integrated and DNA sequences necessary for introduction of the construct into the plant in question (the latter depends on the DNA introduction method to be used).

The choice of regulatory sequences, such as promoter and terminator sequences and optionally signal or transit sequences is determined, eg on the basis of when, where and how the enzyme is desired to be expressed. For instance, the expression of the gene encoding the variant of the invention may be constitutive or inducible, or may be developmental, stage or tissue specific, and the gene product may be targeted to a specific tissue or plant part such as seeds or leaves. Regulatory sequences are eg described by Tague et al, Plant, Phys., 86, 506, 1988.

For constitutive expression the 35S-CaMV promoter may be used (Franck et al., 1980. Cell 21: 285-294). Organ-specific promoters may eg be a promoter from storage sink tissues such as seeds, potato tubers, and fruits (Edwards & Coruzzi, 1990. Annu. Rev. Genet. 24: 275-303), or from metabolic sink tissues such as meristems (Ito et al., 1994. Plant Mol. Biol. 24: 863-878), a seed specific promoter such as the glutelin, prolamin, globulin or albumin promoter from rice (Wu et al., Plant and Cell Physiology Vol. 39, No. 8 pp. 885-889 (1998)), a *Vicia faba* promoter from the legumin B4 and the unknown seed protein gene from *Vicia faba* described by Conrad U. et al, Journal of Plant Physiology Vol. 152, No. 6 pp. 708-711 (1998), a promoter from a seed oil body protein (Chen et al., Plant and cell physiology vol. 39, No. 9 pp. 935-941 (1998), the storage protein napA promoter from *Brassica napus*, or any other seed specific promoter known in the art, eg as described in WO 91/14772. Furthermore, the promoter may be a leaf specific promoter such as the rbcs promoter from rice or tomato (Kyozuka et al., Plant Physiology Vol. 102, No. 3 pp. 991-1000 (1993), the *chlorella* virus adenine methyltransferase gene promoter (Mitra, A. and Higgins, D W, Plant Molecular Biology Vol. 26, No. 1 pp. 85-93 (1994), or the aldP gene promoter from rice (Kagaya et al., Molecular and General Genetics Vol. 248, No. 6 pp. 668-674 (1995), or a wound inducible promoter such as the potato pin2 promoter (Xu et al, Plant Molecular Biology Vol. 22, No. 4 pp. 573-588 (1993).

A promoter enhancer element may be used to achieve higher expression of the enzyme in the plant. For instance, the promoter enhancer element may be an intron which is placed between the promoter and the nucleotide sequence encoding the enzyme. For instance, Xu et al. op cit disclose the use of the first intron of the rice actin 1 gene to enhance expression.

The selectable marker gene and any other parts of the expression construct may be chosen from those available in the art.

The DNA construct is incorporated into the plant genome according to conventional techniques known in the art, including *Agrobacterium*-mediated transformation, virus-mediated transformation, micro injection, particle bombardment, biolistic transformation, and electroporation (Gasser et al, Science, 244, 1293; Potrykus, Bio/Techn. 8, 535, 1990; Shimamoto et al, Nature, 338, 274, 1989).

Presently, *Agrobacterium tumefaciens* mediated gene transfer is the method of choice for generating transgenic dicots (for review Hooykas & Schilperoort, 1992. Plant Mol. Biol. 19: 15-38), however it can also be used for transforming monocots, although other transformation methods are generally used for these plants. Presently, the method of choice for generating transgenic monocots is particle bombardment (microscopic gold or tungsten particles coated with the transforming DNA) of embryonic calli or developing embryos (Christou, 1992. Plant J. 2: 275-281; Shimamoto, 1994. Curr. Opin. Biotechnol. 5: 158-162; Vasil et al., 1992. Bio/Technology 10: 667-674). An alternative method for transformation of monocots is based on protoplast transformation as described by Omirulleh S, et al., Plant Molecular biology Vol. 21, No. 3 pp. 415-428 (1993).

Following transformation, the transformants having incorporated the expression construct are selected and regenerated into whole plants according to methods well-known in the art.

Materials and Methods

Lipase Activity on Tributyrin (LU)

A substrate for lipase is prepared by emulsifying tributyrin (glycerin tributyrate) using gum Arabic as emulsifier. The hydrolysis of tributyrin at 30° C. at pH 7 is followed in a pH-stat titration experiment. One unit of lipase activity (1 LU) equals the amount of enzyme capable of releasing 1 µmol butyric acid/min at the standard conditions.

Lipase Activity on Triolein (SLU)

The lipolytic activity may be determined using olive oil as substrate.

In this SLU method, the lipase activity is measured at 30° C. and pH 9 with a stabilized olive oil emulsion (Sigma catalog No. 800-1) as the substrate, in a 5 mM Tris buffer containing 40 mM NaCl and 5 mM calcium chloride. 2.5 ml of the substrate is mixed with 12.5 ml buffer, the pH is adjusted to 9, 0.5 ml of diluted lipase sample is added, and the amount of oleic acid formed is followed by titration with a pH stat.

One SLU is the amount of lipase which liberates 1 µmole of titratable oleic acid per minute under these conditions.

Phospholipase Activity

The following assay methods were used for qualitative or quantitative determination of phospholipase activity.

Phospholipase Activity (PHLU)

Phospholipase activity (PHLU) is measured as the release of free fatty acids from lecithin. 50 µl 4% L-alpha-phosphatidylcholine (plant lecithin from Avanti), 4% Triton X-100, 5 mM $CaCl_2$ in 50 mM HEPES, pH 7 is added 50 µl enzyme solution diluted to an appropriate concentration in 50 mM HEPES, pH 7. The samples are incubated for 10 min at 30° C. and the reaction stopped at 95° C. for 5 min prior to centrifugation (5 min at 7000 rpm). Free fatty acids are determined using the NEFA C kit from Wako Chemicals GmbH; 25 µl reaction mixture is added 250 µl Reagent A and incubated 10 min at 37° C. Then 500 µl Reagent B is added and the sample is incubated again, 10 min at 37° C. The absorption at 550 nm is measured using an HP 8452A diode array spectrophotometer. Samples are run in at least in duplicates. Substrate and enzyme blinds (preheated enzyme samples (10 min at 95° C.)+substrate) are included. Oleic acid is used as a fatty acid standard. 1 PHLU equals the amount of enzyme capable of releasing 1 µmol of free fatty acid/min at these conditions.

Phospholipase Activity (LEU)

Lecithin is hydrolyzed under constant pH and temperature, and the phospholipase activity is determined as the rate of titrant (0.1N NaOH) consumption during neutralization of the liberated fatty acid.

The substrate is soy lecithin (L-☐-Phosphotidyl-Choline), and the conditions are pH 8.00, 40.0° C., reaction time 2 min. The unit is defined relative to a standard.

Phospholipase Monolayer Assay

On a thoroughly purified surface of a buffer solution (either 10 mM Glycin, pH 9.0 or 10 mM NaOAc, pH 5.0; 1 mM CaCl2, 25° C.) a monolayer of Di-Decanoyl-Phosphatidyl Choline (DDPC) is spread from a chloroform solution. After relaxation of the monolayer (evaporation of chlorofom) the surface pressure is adjusted to 15 mN/m, corresponding to a mean molecular area of DDPC of approx. 63 $Å^2$/molec. A solution containing approximately 60 µg (micro gram) enzyme is injected through the monolayer into the subphase of the re-action compartment (cylinder with surface area 2230 mm2 and reaction volume 56570 mm3) in the "zero-order trough". Enzymatic activity is manifested through the speed of a mobile barrier compressing the monolayer in order to maintain constant surface pressure as insoluble substrate molecules are hydrolyzed into more water soluble reaction products. Having verified that the aqueous solubility of the reaction products (capric acid and MDPC) are considerably higher than for DDPC the number of DDPC-molecules hydrolyzed per minute by the enzyme is estimated from the mean molecular area (MMA) of DDPC. The results are calculated on basis of average barrier speed over the first 5 minutes of hydrolysis.

The result is considered positive for phospholipase if the barrier moves at more than 2 mm/min.

Plate Assay 1

A) 50 ml 2% agarose in purified water is melted/stirred for 5 minutes and cooled to 60-63° C.

B) 50 ml 2% plant L-alpha-Phosphatidylcholine 95% in 0.2M NaOAc, 10 mM $CaCl_2$, pH 5.5 at 60° C. in 30 min. is blended in 15 sec. with ultrathorax.

Equal volumes of 2% agarose and 2% Lecithin (A and B) are mixed, and an equal volume of 1% Triton X-100 is added to this mixture. 250 µl 4 mg/ml crystal violet in purified water is added as indicator. The mixture is poured into appropriate petri dishes (e.g. 30 ml in 14 cm ø dish), and appropriate holes are made in the agar (3-5 mm) for application of enzyme solution.

The enzyme sample is diluted to a concentration corresponding to $0D_{280}$=0.5 and 10 microliter is applied into holes in the agarose/lecithin-matrix. Plates are incubated at 30° C. and reaction zones in the plates are identified after approx. 4-5 hours and/or after approx. 20 hours incubation. The *Humicola lanuginosa* lipase is used as a control, and the presence of a larger clearing zone than the control is taken as a positive result for phospholipase activity.

In a variation of this assay, the addition of Triton X-100 is omitted.

Plate Assay 2

10 g agarose is melted in 550 ml H2O by boiling in a microwave oven. After cooling to 60-70° C. the following ingredients are added:

250 ml of a 0.4 M Citrate buffer (pH 4.5 or pH 7.1)
200 ml 3% lecithin (from Avanti) in 2% Triton-X 100
2 ml 2% crystal violet 30 ml of the mixture is poured into 14 cm ø petri dishes.

The plates are incubated after application of enzyme samples, and the results are interpreted as for Plate assay 1.

Digalactosyl Diglyceride Hydrolyzing (DGDGase) Activity

Monolayer Assay 1

On a thoroughly purified surface of a buffer solution (10 mM NaOAc, pH 5.5; 1 mM CaCl2, 25° C.; 10 mM beta-cyclodextrin (Sigma C-4767)) a monolayer of DGDG (Sigma (D4651)) is spread from a chloroform solution. After relaxation of the monolayer (evaporation of chlorofom) the surface pressure is adjusted to 15 mN/m. A solution containing approximately 60 µg (micro gram) enzyme is injected through the monolayer into the subphase of the re-action compartment (cylinder with surface area 2230 $mm^2$ and reaction volume 56570 $mm^3$) in the "zero-order trough". Enzymatic activity is manifested through increased speed of a mobile barrier compressing the monolayer in order to maintain constant surface pressure as insoluble substrate molecules are hydrolyzed into more water soluble reaction products (in presence of beta cyclodextrin).

The result is considered positive for DGDGase if the barrier moves at more than 1 mm/min.

Monolayer 2

On a thoroughly purified surface of a buffer solution (approx. 75 ml, 10 mM NaOAc, pH 5.5; 1 mM CaCl2, 25° C.; 10 mM beta-cyclodextrin (Sigma C-4767)) a monolayer of DGDG (Sigma (D4651)) is spread from a chloroform solution to a surface pressure of about 30 mN/m. After relaxation of the monolayer (evaporation of chlorofom) a solution containing approximately 30 µg (micro gram) purified enzyme is injected through the monolayer into the 75 ml subphase while surface pressure is measured continuously. Enzymatic activity is manifested through increased rate of decrease in surface pressure as DGDG is hydrolyzed into water soluble reaction products (in presence of beta cyclodextrin).

The result is considered positive for DGDGase if maximal drop in surface pressure (dm/dt) after addition of enzyme exceeds −0.5 mN/min. A number of variants of Lipolase were tested and found to have DGDGase activity, whereas the parent enzyme (Lipolase) only had very limited activity (dπ/dt>−0.5 mN/min.).

Yeast Strain

*Saccharomyces cerevisiae* YNG318: MATa leu2-D2 ura3-52 his4-539 pep4-D1 [cir+], described in WO 97/04079 and WO 97/07205.

Transformation of Yeast Strain

The DNA fragments and the opened vectors are mixed and transformed into the yeast *Saccharomyces cerevisiae* YNG318 by standard methods.

Vector for Yeast Transformation pJSO026 (*S. cerevisiae* expression plasmid) is described in WO 97/07205 and in J. S. Okkels, (1996) "A URA3-promoter deletion in a pYES vector increases the expression level of a fungal lipase in *Saccharomyces cerevisiae*. Recombinant DNA Biotechnology III: The Integration of Biological and Engineering Sciences, vol. 782 of the Annals of the New York Academy of Sciences). It is derived from pYES 2.0 by replacing the inducible GAL1-promoter of pYES 2.0 with the constitutively expressed TPI (triose phosphate isomerase)-promoter from *Saccharomyces cerevisiae* (Albert and Karwasaki, (1982), J. Mol. Appl Genet., 1, 419-434), and deleting a part of the URA3 promoter.

Site-Directed Mutagenesis

For the construction of variants of a *H. lanuginosa* lipolytic enzyme the commercial kit, Chameleon double-stranded, site-directed mutagenesis kit can be used according to the manufacturer's instructions.

The gene encoding the lipolytic enzyme in question is inserted into the plasmid pHD414. In accord-ance with the manufacturer's instructions the ScaI site of the Ampicillin gene of pHD414 is changed to a MluI site by use of the following primer:

```
Primer 3:
                                           (SEQ ID NO. 27)
   AGAAATCGGGTATCCTTTCAG.
```

The pHD414 vector comprising the lipolytic gene in question is then used as a template for DNA polymerase and oligos 7258 and 7770.

```
7258:
                                           (SEQ ID NO. 28)
   5'p gaa tga ctt ggt tga cgc gtc acc agt cac 3'
```

(Thus changing the ScaI site found in the ampicillin resistance gene and used for cutting to a MluI site).

Primer no. 7770 was used as the selection primer.

```
7770:
                                           (SEQ ID NO. 29)
   5'p tct agc cca gaa tac tgg atc aaa tc 3'
```

(Changes the ScaI site found in the *H. lanuginosa* lipase gene without changing the amino acid sequence).

The desired mutation (e.g. in the N-terminal of the lipolytic gene or the introduction of a cystein residue) is introduced into the lipolytic gene in question by addition of an appropriate oligos comprising the desired mutation.

PCR reactions are performed according to the manufacturer's recommendations.

Screening Method

The yeast libraries are spread on cellulose filters on SC-ura agar plates and incubated for 3-4 days at 30° C.

The filters are then transferred to the lecithin plates and incubated at 37° C. for 2-6 hours. Yeast cells harboring active phospholipases will develop white clearing zones around the colonies. The positive variants can then be further purified and tested.

Media

SC-ura Medium

| Yeast Nitrogen (without amino aicds) | 7.5 g |
| Succinic acid | 11.3 g |
| NaOH | 6.8 g |
| Casaminoacid (without vitamins) | 5.6 g |
| Tryptophan | 0.1 g |
| Agar, Merck | 20 g |
| Distilled water | ad 1000 ml |

Autoclaved for 20 minutes at 121° C.

From a sterile stock solution of 5% Threonine 4 ml is added to a volume of 900 ml together with 100 ml of a sterile 20% glucose.

EXAMPLES

Example 1

Construction of Variants with the Backbone from *Humicola lanuginosa* Lipase and C-terminal from *Fusarium Oxysporum* Phospholipase by PCR Reaction The following variants were used as templates for the backbone from the *Humicola lanuginosa* lipase: E1A+G91A+D96W+E99K+Q249R and SPIRR+G91A+D96W+E99K+Q249R. The parent lipase was used for generating a fragment in the C-terminal without Q249R. The template for the C-terminal phospholipase was the *Fusarium oxysporum* phospholipase, cloned in the same vector as the variants of *Humicola lanuginosa* lipase.

PCR reaction 1: 4244 (SEQ ID NO: 1) as 5' primer and H7 (SEQ ID NO: 6) as 3' primer and one of the two templates mentioned above.

PCR reaction 2: FOL14 (SEQ ID NO: 3) as 5' primer and FOL15 (SEQ ID NO: 4) as 3' primer and *Humicola lanuginosa* lipase as template (no mutation in pos 249)

PCR reaction 3: FOL16 (SEQ ID NO: 5) as 5' primer and AP (SEQ ID NO: 2) as 3' primer and F.o. phospholipase as template A PCR reaction 4 was made to create the connection between the *Humicola lanuginosa* lipase variant and the C-terminal from the phospholipase by using FOL14 (SEQ ID NO: 3) as 5' primer and AP (SEQ ID NO: 2) as 3' primer and PCR reaction 2 and 3 as template.

The final PCR was made with 4244 (SEQ ID NO: 1) as 5' primer and KBoj14 (SEQ ID NO: 7) as 3' primer and PCR re-action 1 and 4 as template (by using *Humicola lanuginosa* lipase as template in reaction 2 a possibility to omit the mutation in position 249 was created).

The final PCR fragment was used in an in vivo recombination in yeast together with pJSO026 cut with the restriction enzymes. SmaI (or BamHI) and XbaI (to remove the coding region and at the same time create an overlap of about 75 bp in each end to make a recombination event possible). This final treatment was also used in the following examples.

Primer FOL14 (SEQ ID NO: 3) and primer 15/16 are mixed oligoes to give the possibility to bind both with *Humicola lanuginosa* lipase and phospholipase templates and at the same time give possibilities for introducing the amino acids from both templates in the different positions. For some of the positions new amino acids could be introduced as well.

Primer FOL14 (SEQ ID NO: 3)
Position 205 in the *H. lanuginosa* lipase: 75% R, 25% S
Primer FOL15 (SEQ ID NO: 4)/FOL16 (SEQ ID NO: 5)
Position 256 in the *H. lanuginosa* lipase: 50% P, 50% A
Position 260 in the *H. lanuginosa* lipase: 25% R, 12.5% Q, 12.5% H, 12.5% C, 12.5% Y, 12.5% W, 12.5% stop.

The sequences of the resulting variants were determined, and were found to correspond to *Humicola lanuginosa* lipase with the following alterations. Alterations in parentheses are uncertain.

E1A, G91A, D96W, E99K, P256A, W260H, G263Q, L264A, I265T, G266D, T267A, L269N, 270A, 271G, 272G, 273F, (274S)

E1A, G91A, D96W, E99K, E239C, Q249R, P256A, G263Q, L264A, I265T, G266D, T267A, L269N, 270A, 271G, 272G273F, (274S)

E1A, G91A, D96W, E99K, N248T, Q249R, W260Q, G263Q, L264A, I265T, G266D, T267A, L269N, 270A, 271G, 272G, 273F, (274S)

SPIRR (SEQ ID NO. 21), G91A, D96W, E99K, W260C, G263Q, L264A, I265T, G266D, T267A, L269N, 270A, 271G, 272, G273F, (274S)

SPIRR (SEQ ID NO. 21), G91A, D96W, E99K, G263Q, L264A, I265T, G266D, T267A, L269N, 270A, 271G, 272G, 273F, (274S)

E1A, G91A, D96W, E99K, G263Q, L264A, I265T, G266D, T267A, L269N, 270A, 271G, 272G, 273F, (274S)

Example 2

Production of Truncated Sequences

Variants were made with stop after amino acid 269, 270, 271, 272, (273 and 274)

The following PCR reactions were made with the following template: E1A, G91A, D96W, E99K, P256A, W260H, G263Q, L264A, I265T, G266D, T267A, L269N, 270A, 271G, 272G, 273F, (274S).

Reaction 1: 5' primer 4244 (SEQ ID NO: 1) and 3' primer KBoj36 (stop after 269)
Reaction 2: 5' primer 4244 (SEQ ID NO: 1) and 3' primer KBoj37 (stop after 270)
Reaction 3: 5' primer 4244 (SEQ ID NO: 1) and 3' primer KBoj38 (stop after 271)
Reaction 4: 5' primer 4244 (SEQ ID NO: 1) and 3' primer KBoj39 (stop after 272)

The sequences of the resulting variants were determined, and were found to correspond to *Humicola lanuginosa* lipase with the following alterations:

E1A, G91A, D96W, E99K, P256A, W260H, G263Q, L264A, I265T, G266D, T267A, L269N

E1A, G91A, D96W, E99K, P256A, W260H, G263Q, L264A, I265T, G266D, T267A, L269N, 270A

E1A, G91A, D96W, E99K, P256A, W260H, G263Q, L264A, I265T, G266D, T267A, L269N, 270A, 271G

E1A, G91A, D96W, E99K, P256A, W260H, G263Q, L264A, I265T, G266D, T267A, L269N, 270A, 271G, 272G

Example 3

Removal of Mutations in the Lid Region

G91A or E99K can be removed without loosing the phospholipase activity. The sequences of the resulting variants were determined, and were found to correspond to *Humicola lanuginosa* lipase with the following alterations:

E1A, G91A, D96W, P256A, W260H, G263Q, L264A, I265T, G266D, T267A, L269N, 270A, 271G, 272G, 273F, (274S)

SPIRR (SEQ ID NO. 21), D96W, E99K, G263Q, L264A, I265T, G266D, T267A, L269N, 270A, 271G, 272G, 273F, (274S)

SPIRR (SEQ ID NO. 21), G91A, D96W, G263Q, L264A, I265T, G266D, T267A, L269N, 270A, 271G, 272G, 273F, (274S)

E1A, G91A, D96W, P256A, W260H, G263Q, L264A, I265T, G266D, T267A, L269N, 270A, 271G, 272G, 273F, (274S)

Example 4

Doping in the C-Terminal Region of *Humicola lanuginosa* Lipase to Introduce Phospholipase Activity Three different libraries were constructed with possibilities for mutations in position 256 and position 263-269. At the same time possibilities for extension of the C-terminal with either 1, 2, 3 or 4 amino acids were included.

Doping, the wt sequences are underlined:
256: P 94, A 3, T 3
263: G 87, E 4.8, A 3.8, R 3.6, Q 0.2, P 0.2
264: L 87, P 4.8, Q 3.8, V 3.6, A 0.2, E 0.2
265: I 85, T 5.6, L 2.2, S 1.6, N 1.5, F 1.4, R 0.4, K 0.4 A, P 0.1, G, D, C, H, Y 0.03, Q, E 0.01, stop 0.016
266: G 86, D 5.9, R 2, S 1.7, C 1.6, A 0.9, V 0.9, E 0.7, W 0.2, H, Y 0.1, I,L,T,F,P 0.02, Q,K 0.01, stop 0.014
267: T 86, A 6.6, S 1.9, R 0.9, N 0.9, 10.9, K 0.9, M 0.9, P 0.9, P 0.9, G,V 0.14, D,E 0.07, L 0.03, C,Q,H,F,W,Y 0.01, stop 0.01
268: C 91, S 1.9, R 1.0, G 1.0, F 0.9, Y 0.9, L 0.04, A,N,D,H,I,P,T,V 0.01, stop 2.8
269: L 92, stop 8 (KBoj 32 (SEQ ID NO: 8) and KBoj33)/N 86, K 2.7, D 1.8, H 1.8, I 1.8, S 1.8, T 1.9, Y 1.8, R 0.1, Q,M,E 0.06, A,C,G,L,F,P,V 0.04, stop 0.06 (KBoj34)

270: stop 100 (KBoj33)/A 44, P 44, S 1.9, T 1.8, R 1.5, L 1.5, G 1.4, V 1.4, D 0.7, Q 0.7, E 0.7, H 0.7, N,C,I,K,M,F,W,Y 0.03, stop 0.03 (KBoj 32 (SEQ ID NO: 8) and KBoj 34)

271: G 72, R 4.5, V 3.2, E 3.0, C 2.9, A 1.6, S 1.2, D 1.0, L 0.5, I,K,Y 0.15, Q,T 0.08, N,P 0.05, stop 9.2

272: G 72, R 4.5, V 3.2, E 3.0, C 2.9, A 1.6, S 1.2, D 1.0, L 0.5, I,K,Y 0.15, Q,T 0.08, N,P 0.05, stop 9.2

273: F 74, L 11, S 2.8, I 2.7, V 2.7, Y 2.5, C 2.5, A,R,T 0.1, N,D,H 0.08, Q,E,K 0.01, stop 0.5

274 STOP

Library A: PCR reaction with 4244 (SEQ ID NO: 1) as 5' primer and KBoj 33 as 3' primer and E1A+G91A+D96W+E99K+Q249R or E1A+G225R as template. Variants from this library will be without extension.

Library B: PCR reaction with 4244 (SEQ ID NO: 1) as 5' primer and KBoj 32 (SEQ ID NO: 8) as 3' primer and E1A+G91A+D96W+E99K+Q249R or E1A+G225R as template. Variants from this library will most probably contain a C-terminal extension but can contain stop codons before the extension.

Library C: PCR reaction with 4244 (SEQ ID NO: 1) as 5' primer and KBoj 34 as 3' primer and E1A+G91A+D96W+E99K+Q249R or E1A+G225R as template. Variants from this library will most probably contain mutations in position 269 and a C-terminal extension but can contain stop codons before the extension.

The following variants were obtained:
Library A:
  E1A+G91A+D96W+E99K+Q249R+G266D
Library B:
  E1A+G91A+D96W+E99K+(R232L)+Q249R+G266S+270A
  E1A+G91A+D96W+E99K+Q249R+G266S+270D+271G
  E1A+G91A+D96W+E99K+Q249R+L264G+I265G+G266F+T267stop
  E1A+G91A+D96W+E99K+Q249R+G266A+270P+271G
  E1A+G91A+D96W+E99K+Q249R+L264P+I265F+L269stop
Library C:
  E1A+G91A+D96W+E99K+Q249R+G263E+G266D+L269N+270P+271V+272G+273F
  E1A+G91A+D96W+E99K+Q249R+G263A+G266S+L269N+270A+271G+272R+273F
  E1A+G91A+D96W+E99K+Q249R+L264P-G266+L269I+270P+271R+272G+273F
  E1A+G91A+D96W+E99K+Q249R+G266D+L269S+270A+271G+272G+273F
  E1A+D27G+G91A+D96W+E99K+Q249R+G266S+L269N+270A+271G+272G+273F
  E1A+G91A+D96W+E99K+Q249R+G266D+L269N+270A E1A+G91A+D96W+E99K+Q249R+L264P+L267Q+L269N
  E1A+G91A+D96W+E99K+Q249R+G263R+I265L+L269N+270P Example 5

For some of the above variants, the pH optimum for lipase and phospholipase was determined by using the LU and PHLU methods at various pH values. The results showed that the pH optimum phospholipase activity was in the range 4-6. The optimum for lipase activity varied from about pH 6 to about pH 10.

8 variants listed in Example 5 were analyzed for phospholipase activity by the mono layer assay described above at pH 5 and 9. The results showed that all the variants have phospholipase activity at pH 5 and 9, whereas the parent lipase (*Humicola lanuginosa* lipase) showed no activity at pH 5 or 9. Depending on the variant, the activity at pH 5 was higher or lower than at pH 9.

A prior-art variant of *Humicola lanuginosa* lipase was found to have no phospholipase activity at pH 5: SPIRR+N94K+F95L+D96H+N101S+F181L+D234Y+I252L+P256T+G263A+L264Q.

Example 5

Variants of *Humicola* Lipase with Phospholipase Activity

Variants of the parent lipase from *Humicola lanuginosa* were prepared and tested for phospholipase activity as described above. The following variants were found to have phospholipase activity, where as the parent had no phospholipase activity by the same method.

E1A, G91A, D96W, E99K, P256A, W260H, G263Q, L264A, I265T, G266D, T267A, L269N, 270A, 271G, 272G, 273F, (274S)

SPIRR (SEQ ID NO. 21), G91A, D96W, E99K, G263Q, L264A, I265T, G266D, T267A, L269N, 270A, 271G, 272G, 273F, (274S)

E1A, G91A, D96W, P256A, W260H, G263Q, L264A, I265T, G266D, T267A, L269N, 270A, 271G, 272G, 273F, (274S)

E1A, G91A, D96W, E99K, P256A, W260H, G263Q, L264A, I265T, G266D, T267A, L269N

E1A, G91A, D96W, E99K, Q249R, G266S, 270D, 271G

E1A, G91A, D96W, E99K, Q249R, G266D

E1A, G91A, D96W, E99K, Q249R, G266A, 270P, 271G

G266D

E1SPPCGRRP (SEQ ID NO. 25)+E99N+E239C+Q249R+G266D

E1SPPCGRRP (SEQ ID NO. 25)+E239C+Q249R+G266D

E1SPPCGRRP (SEQ ID NO. 25)+L93K+E99K+E239C+Q249R+G266D

E1SPPCGRRP (SEQ ID NO. 25)+E99K+E239C+Q249R+G266D

G266A
G266W
G266V
G263Q+L264A+I265T+G266D+T267A
G263F+L264A+G266S+T267E
E1SPPCGRRP (SEQ ID NO. 25)+E239C+Q249R+G263Q+L264A+I265T+G266D+T267A
G266S
G266L
G263A+G266A
G263A+G266Y
E1SPPCGRRP (SEQ ID NO. 25)+E239C+Q249R+G266A
E1SPPCGRRP (SEQ ID NO. 25)+E239C+Q249R+G266S
E1SPPCGRRP (SEQ ID NO. 25)+E239C+Q249R+G263F+L264A+G266S+T267E
D62A+G266A
D62A+G266S
D96S+G266A
D96S+G266S
D96S+G266R
D96S+G266W
D96S+G266V

E1SPPCGRRP (SEQ ID NO. 25)+G91A+D96W+ E239C+Q249R+G266D
E1SPPCGRRP (SEQ ID NO. 25)+G91A+D96W+ E239C+Q249R+G266S
E1SPPCGRRP (SEQ ID NO. 25)+G91A+D96W+ E239C+Q249R+G263E+G266S+270A
E1SPPCGRRP (SEQ ID NO. 25)+G91A+D96W+ E239C+Q249R+L264P+G266S
E1SPPCGRRP (SEQ ID NO. 25)+G91A+D96W+ E239C+Q249R+P256T+G266D
E1SPPCGRRP (SEQ ID NO. 25)+G91A+D96W+ E239C+Q249R+G266C+T267P+L269stop
G263D+L264+I265N+G266E+T267GS
E219G+L264I+I265N+G266T+T267GL
E1A+G91A+D96W+E99K+P256A+W260H+ G263Q+ L264A+I265T+G266D+T267A+L269N+270A+271G+ 272G+273F (+274S)
E1A+G91A+D96W+E99K+E239C+Q249R+P256A+ G263Q+L264A+I265T+G266D+T267A+L269N+270A+ 271G+272G+273F (+274S)
E1A+G91A+D96W+E99K+N248T+Q249R+W260Q+ G263Q+L264A+I265T+G266D+T267A+L269N+270A+ 271G+272G+273F (+274S)
SPIRR (SEQ ID NO. 21)+G91A+D96W+E99K+W260C+ G263Q+L264A+I265T+G266D+T267A+L269N+270A+ 271G+272+G273F (+274S)
SPIRR (SEQ ID NO. 21)+G91A+D96W+E99K+G263Q+ L264A+I265T+G266D+T267A+L269N+270A+271G+ 272G+273F (+274S)
E1A+G91A+D96W+E99K+G263Q+L264A+I265T+ G266D+T267A+L269N+270A+271G+272G+273F (+274S)
E1A+G91A+D96W+E99K+P256A+W260H+ G263Q+ L264A+I265T+G266D+T267A+L269N+270A+271G+ 272G+273F (+274S)
SPIRR (SEQ ID NO. 21)+D96W+E99K+G263Q+ L264A+I265T+G266D+T267A+L269N+270A+271G+ 272G+273F (+274S)
SPIRR (SEQ ID NO. 21)+G91A+D96W+G263Q+ L264A+I265T+G266D+T267A+L269N+270A+271G+ 272G+273F (+274S)
E1A+G91A+D96W+E99K+P256A+W260H+ G263Q+ L264A+I265T+G266D+T267A+L269N
E1A+G91A+D96W+E99K+Q249R+G263E+G266D+ L269N+270P+271V+272G+273F
E1A+G91A+D96W+E99K+Q249R+G263A+G266S+ L269N+270A+271G+272R+273F
E1A+G91A+D96W+E99K+Q249R+L264P+4266+ L269I+270P+271R+272G+273F
E1A+G91A+D96W+E99K+Q249R+L264C+I265N+ G266P+T267stop
E1A+G91A+D96W+E99K (+R232L)+Q249R+G266S+ 270A
E1A+G91A+D96W+E99K+Q249R+G266S+270D+ 271G
E1A+G91A+D96W+E99K+Q249R+L264F+Δ266+ 270A+271G+272G+273F
E1A+G91A+D96W+E99K+Q249R+L264G+I265G+ G266F+T267stop
E1A+G91A+D96W+E99K+Q249R+L264stop
E1A+G91A+D96W+E99K+P256A+W260H+ G263Q+ L264A+I265T+G266D+T267A+L269N+270A+271G
E1A+G91A+D96W+E99K+P256A+W260H+ G263Q+ L264A+I265T+G266D+T267A+L269N+270A+271G+ 272G
E1A+G91A+D96W+E99K+Q249R+G266D
E1A+G91A+D96W+E99K+Q249R+G266D
E1A+G91A+D96W+E99K+Q249R+G266A+270P+ 271G
E1A+G91A+D96W+E99K+Q249R+L264P+I265F+ L269stop
E1A+G91A+D96W+E99K+Q249R+G266D+L269S+ 270A+271G+272G+273F
E1A+G91A+D96W+E99K+Q249R+G266D+L269N+ 270A
E1A+G91A+D96W+E99K+Q249R+G266S+L269N+ 270A+271G+272G+273F
E1A+G91A+D96W+E99K+Q249R+L264P+L267Q+ L269N
E1A+G91A+D96W+E99K+Q249R+G263R+I265L+ L269N+270P
E1A+D96W+E99K+P256A+W260H+ G263Q+L264A+ I265T+G266D+T267A+L269N+270A+271G+272G+273F (+274S)
E1A+G225R+G266D
E1A+G225R+G263A+I265V+G266S
E1A+G225R+G263A+T267A
E1SPPCGRRP (SEQ ID NO. 25)+D96S+E239C+ Q249R+I252M+L264Q+G266D
E1SPPCGRRP (SEQ ID NO. 25)+G91A+D96W+ E239C+Q249R+G266D
E1SPPCGRRP (SEQ ID NO. 25)+D96S+E239C+ Q249R+G266D
E1SPPCGRRP (SEQ ID NO. 25)+D96S+E239C+ Q249R+G266C+L267A
E1A+G91A+D96W+E99K+Q249R+G266A
E1A+D96M+G106S+G225R+G266D
E1A+D96Q+G106S+G225R+G266S
E1A+D96F+G225R+G266S
E1A+D96C+G225R+G266T
E1A+D96H+ G106S+G225R+G266S
SPIRR (SEQ ID NO. 21)+D96S+G266D
SPIRR (SEQ ID NO. 21)+D96R+G106S+G266D
SPIRR (SEQ ID NO. 21)+D96I+G106S+G266S
SPIRR (SEQ ID NO. 21)+D96W+K237R+G266S
SPIRR (SEQ ID NO. 21)+G266A
SPIRR (SEQ ID NO. 21)+D96S+G106S+G225R+G266D
SPIRR (SEQ ID NO. 21)+D96Q+G106S+G225R+G266A
SPIRR (SEQ ID NO. 21)+D96Y+G106S+G225R+G266N
SPIRR (SEQ ID NO. 21)+D96C+G106S+G225R+G266T
SPIRR (SEQ ID NO. 21)+D96H+ T186I+G225R+G266S
E1SPPRRP (SEQ ID NO. 23)+G91A+D96W+E239C+ Q249R+G266D
E1SPPRRP (SEQ ID NO. 23)+G91A+D96W+E239C+ Q249R+G266S
E1SPPRRP (SEQ ID NO. 23)+G91A+D96W+E239C+ Q249R+G263E+G266S+270A
E1SPPRRP (SEQ ID NO. 23)+G91A+D96W+E239C+ Q249R+L264P+G266S
E1SPPRRP (SEQ ID NO. 23)+G91A+D96W+E239C+ Q249R+P256T+G266D
E1SPPRRP (SEQ ID NO. 23)+G91A+D96W+E239C+ Q249R+G266C+T267P+L269stop
E1A+G91A+D96W+E99K+Q249R+G266S+T267S
E1SPPCGRRP (SEQ ID NO. 25)+G91A+D96W+ E239C+Q249R+P256T+G266S
E1SPPCGRRP (SEQ ID NO. 25)+E239C+Q249R+ P256T+G266S+T267A
E1SPPCGRRP (SEQ ID NO. 25)+E239C+Q249R+ G266D
E1SPPCGRRP (SEQ ID NO. 25)+G91A+D96W+ E239C+Q249R+G266D
E1SPPRRP (SEQ ID NO. 23)+D96S+E239C+Q249R+ G266D L259S
G266D
G91A+D96W+E99K+G263Q+L264A+I265T+G266D+T267A+L269N+270A+271G+272G+273F (+274S)
G266E
G263A+G266A
E1SPCRPRP (SEQ ID NO. 26)+E239C+Q249R+G266A
E1SPCRPRP (SEQ ID NO. 26)+E239C+Q249R+G266S
D96S+G266A
D96S+G266S
D96S+G266W
E1SPPCGRRP (SEQ ID NO. 23)+D96S+E239C+Q249R+G263D+L264I+I265N+G266E+T267GS
E1SPPCGRRP (SEQ ID NO. 23)+D96S+E239C+Q249R+L264I+I265N+G266T+T267GL
D96F+G266A
D96F+G266S
E1SPPCGRRP (SEQ ID NO. 23)+E99N+E239C+Q249R+G266A
E1SPPCGRRP (SEQ ID NO. 23)+D96S+E239C+Q249R+G266A
E1SPPCGRRP (SEQ ID NO. 23)+D96S+E239C+Q249R+G266S
E1SPPCGRRP (SEQ ID NO. 23)+D96S+E239C+Q249R+G263F+L264A+G266S+T267E
V60G+D62A+S83T+R84K+D96W+G266D
V60G+D62A+S83T+D96W+G266D
V60G+D62A+S83T+D96W+G266W
L259I
L259N
D96W+G263Q+L264A+I265T+G266D+T267A In the table above, (+274S) indicates that the presence of this amino acid residue at the C-terminal is uncertain. For one such variant, it was found that only a minor fraction contained this residue Several of the above variants had a higher ratio of phospholipase (PHLU) to lipase (LU) than a prior-art enzyme from *F. oxysporum* known to have both lipase and phospholipase activity.

For some of the above variants, the pH optimum for lipase and phospholipase was determined by using the LU and PHLU methods at various pH values. The results showed that the pH optimum phospholipase activity was in the range 4-6. The optimum for lipase activity varied from about pH 6 to about pH 10.

8 variants listed in Example 5 were analyzed for phospholipase activity by the mono layer assay described above at pH 5 and 9. The results showed that all the variants have phospholipase activity at pH 5 and 9, whereas the parent lipase (*Humicola lanuginosa* lipase) showed no activity at pH 5 or 9. Depending on the variant, the activity at pH 5 was higher or lower than at pH 9.

A prior-art variant of *Humicola lanuginosa* lipase was found to have no phospholipase activity at pH 5: SPIRR+N94K+F95L+D96H+N101S+F181L+D234Y+I252L+P256T+G263A+L264Q.

The following variants of the parent lipase from *Humicola lanuginosa* may also have phospholipase activity:
D62A+S83T+D96W+G266S
G91A+D96W+E99K+G263Q+L264A+I265T+G266D+T267A+L269N+270A+271G+272G+273F+274S
G91A+D96L+E99K+G263Q+L264A+I265T+G266D+T267A+L269N+270A+271G+272G+273F+274S
G91A+D96N+E99K+G263Q+L264A+I265T+G266D+T267A+L269N+270A+271G+272G+273F+274S
G91A+D96A+E99K+G263Q+L264A+I265T+G266D+T267A+L269N+270A+271G+272G+273F+274S
G91A+D96E+E99K+G263Q+L264A+I265T+G266D+T267A+L269N+270A+271G+272G+273F+274S
G91A+D96S+E99K+G263Q+L264A+I265T+G266D+T267A+L269N+270A+271G+272G+273F+274S
G91A+D96R+E99K+G263Q+L264A+I265T+G266D+T267A+L269N+270A+271G+272G+273F+274S
G91A+D96G+E99K+G263Q+L264A+I265T+G266D+T267A+L269N+270A+271G+272G+273F+274S
G91A+D96Q+E99K+G263Q+L264A+I265T+G266D+T267A+L269N+270A+271G+272G+273F+274S
G91A+D96F+E99K+G263Q+L264A+I265T+G266D+T267A+L269N+270A+271G+272G+273F+274S
G91A+D96W+E99K+G263Q+L264A+I265T+G266S+T267A+L269N+270A+271G+272G+273F+274S
G91A+D96F+E99K+G263Q+L264A+I265T+G266S+T267A+L269N+270A+271G+272G+273F+274S+
R84W+G91A+D96W+E99K+G263Q+L264A+I265T+G266S+T267A+L269N+270A+271G+272G+273F+274S
R84W+G91A+D96F+E99K+G263Q+L264A+I265T+G266S+T267A+L269N+270A+271G+272G+273F+274S+
R84W+G91A+D96F+E99K+G263Q+L264A+I265T+G266D+T267A+L269N+270A+271G+272G+273F+274S
G91A+D96F+G263Q+L264A+I265T+G266S+T267A+L269N+270A+271G+272G+273F+274S
G91A+D96W+G263Q+L264A+I265T+G266S+T267A+L269N+270A+271G+272G+273F+274S
G91A+D96F+G263Q+L264A+I265T+G266D+T267A+L269N+270A+271G+272G+273F+274S
G91A+D96W+G263Q+L264A+I265T+G266D+T267A+L269N+270A+271G+272G+273F+274S Example 6

Variants of *Rhizomucor* Lipase with Phospholipase Activity

The following two variants of the parent lipase from *Rhizomucor miehei* were prepared and tested for phospholipase activity as described above. The variants were found to have phospholipase activity, where as the parent had no phospholipase activity by the same method.
G266N
G266V Example 7

Variants of *Humicola* Lipase with Increased Specificity for Long-Chain Fatty Acids Variants of the parent lipase from *Humicola lanuginosa* were prepared and tested for their hydrolytic activity on two triglyceride substrates with different chain length: tributyrin ($C_{4:0}$) and triolein ($C_{18:1}$). The tests were done at pH 9 by the LU and SLU methods described above. The following variants were found to have a higher ratio of triolein activity to tributyrin activity than the parent enzyme (*Humicola lanuginosa* lipase):
E1SPIRPRP (SEQ ID NO. 22)+G91A+D96N+E99K+Q249R
E1SPCRPRP (SEQ ID NO. 26)+S83T+N94K+D96L+E239C+Q249R
G266D
E1SPIRPRP (SEQ ID NO. 22)+D62A+E99K+Q249R
E1SPIRPRP (SEQ ID NO. 22)+D62G+E99K+Q249R
E1SPIRPRP (SEQ ID NO. 22)+D62V+E99K+Q249R
E1SPIRPRP (SEQ ID NO. 22)+R84W+E99K+Q249R
E1SPIRPRP (SEQ ID NO. 22)+R84K+E99K+Q249R E1SPIRPRP (SEQ ID NO. 22)+K98D+E99K+Q249R
E1SPIRPRP (SEQ ID NO. 22)+E99K+Q249R+270PGLPFKRV
E1SPPCGRRP (SEQ ID NO. 25)+E99N+N101S+T231K+R232G+D234G+E239C+Q249R
E1SPIRPRP (SEQ ID NO. 22)+E99K+Q249R+270PWPARLGRL
L93K+D96G
G91A+D96W+E99K+G263Q+L264A+I265T+G266D+T267A+L269N+270A+271G+272G+273F (+274S)
E1SPCRPRP+V60G+E99N+S119G+R209P+E239C+Q249R
G266A
G266E
G266V
G263Q+L264A+I265T+G266D+T267A
G266L
G263A+G266A
E1SPCRPRP (SEQ ID NO. 26)+E239C+Q249R+G266A
E1SPCRPRP (SEQ ID NO. 26)+E239C+Q249R+G266S
D96S+G266A
D96S+G266S
D96S+G266W
L264I+I265N+G266T+T267GL
E1SPPCGRRP (SEQ ID NO. 25)+D96S+E239C+Q249R+L264+I265N+G266T+T267GL
D96F+G266A
D96F+G266S
E1SPPCGRRP (SEQ ID NO. 25)+E99N+E239C+Q249R+G266A
E1SPPCGRRP (SEQ ID NO. 25)+D96S+E239C+Q249R+G266A
E1SPPCGRRP (SEQ ID NO. 25)+D96S+E239C+Q249R+G266S
D62A+S83T
E1SPPCGRRP (SEQ ID NO. 25)+K98D+E99N+E239C+Q249R
T231R+N233R+270CP
E1SPPCGRRP (SEQ ID NO. 25)+E99N+E239C+Q249R+270MD

E1SPPCGRRP (SEQ ID NO. 25)+D62A+S83T+E99N+E239C+Q249R

D62A+S83T+G91A+E99K+T231R+N233R+Q249R

V60G+D62A+S83T+R84K+D96W+G266D

L259N

L259R

L259M

L259Q

SPPCGRRP(-E) (SEQ ID NO. 25)+R84W+E99N+N101S+E239C+Q249R

R84W+G91A+E99K+T231R+N233R+Q249R

Y21I

Y21V

SPIRPRP(-E) (SEQ ID NO. 22)+R84L+E99K+Q249R

Y21C

SPIRPRP(-E) (SEQ ID NO. 22)+D62+E99K+Q249R

D96W+G263Q+L264A+I265T+G266D+T267A+L269N+A270+G271+G272+F273+S274.

G91A+D96W+E99K+G263Q+L264A+I265T+G266D+T267A+L269N+270A+271G+272G+273F+274S

The following variants of the parent lipase from *Humicola lanuginosa* may also have an increased specificity for long-chain fatty acids:

SPIRPRP(-E) (SEQ ID NO. 22)+V60R+D62V+L93K+E99K+Q249R

SPIRPRP(-E) (SEQ ID NO. 22)+D62V+E99K+Q249R

SPIRPRP(-E) (SEQ ID NO. 22)+E99K+Q249R+P256D

SPIRPRP(-E) (SEQ ID NO. 22)+D62V+E99K+Q249R+P256D

SPIRPRP(-E) (SEQ ID NO. 22)+D62V+E99K+Q249R+P256S

G91A+D96W+E99K+G263Q+L264A+I265T+G266D+T267A+L269N+270A+271G+272G+273F+274S

G91A+D96L+E99K+G263Q+L264A+I265T+G266D+T267A+L269N+270A+271G+272G+273F+274S

G91A+D96N+E99K+G263Q+L264A+I265T+G266D+T267A+L269N+270A+271G+272G+273F+274S

G91A+D96A+E99K+G263Q+L264A+I265T+G266D+T267A+L269N+270A+271G+272G+273F+274S

G91A+D96E+E99K+G263Q+L264A+I265T+G266D+T267A+L269N+270A+271G+272G+273F+274S

G91A+D96S+E99K+G263Q+L264A+I265T+G266D+T267A+L269N+270A+271G+272G+273F+274S

G91A+D96R+E99K+G263Q+L264A+I265T+G266D+T267A+L269N+270A+271G+272G+273F+274S

G91A+D96L+E99K+G263Q+L264A+I265T+G266D+T267A+L269N+270A+271G+272G+273F+274S

G91A+D96Q+E99K+G263Q+L264A+I265T+G266D+T267A+L269N+270A+271G+272G+273F+274S

G91A+D96F+E99K+G263Q+L264A+I265T+G266D+T267A+L269N+270A+271G+272G+273F+274S

G91A+D96W+E99K+G263Q+L264A+I265T+G266S+T267A+L269N+270A+271G+272G+273F+274S

G91A+D96F+E99K+G263Q+L264A+I265T+G266S+T267A+L269N+270A+271G+272G+273F+274S

R84W+G91A+D96W+E99K+G263Q+L264A+I265T+G266S+T267A+L269N+270A+271G+272G+273F+274S

R84W+G91A+D96F+E99K+G263Q+L264A+I265T+G266S+T267A+L269N+270A+271G+272G+273F+274S

R84W+G91A+D96F+E99K+G263Q+L264A+I265T+G266D+T267A+L269N+270A+271G+272G+273F+274S

SPPCGRRP(-E) (SEQ ID NO. 25)+V60G+D62E+S83T+R84K+E99N+N101S+E239C+Q249R

V60G+D62E+S83T+R84K+G91A+E99K+T231R+N233R+Q249R

Example 8

Variants of *Fusarium* Lipase with Increased Specificity for Long-Chain Fatty Acids Variants of the parent lipase from *Fusarium oxysporum* were prepared and tested as in the previous example. The following variants were found to have a higher ratio of triolein activity to tributyrin activity than the parent enzyme:

Y23S

Y260L

The following variants of the parent lipase from *Fusarium oxysporum* may also have an increased specificity for long-chain fatty acids:

R80H+S82T

S82T+A129T

Example 9

Variants of *Rhizomucor* Lipase with Increased Specificity for Long-Chain Fatty Acids The following variants of the parent lipase from *Rhizomucor miehei* may have an increased specificity for long-chain fatty acids:

Y260W

Y28L

Y28C+H217N

Example 10

Variants of *Humicola* Lipase with Increased Specificity for Short-Chain Fatty acids Variants of the parent lipase from *Humicola lanuginosa* were prepared and tested as in the previous example. The following variants were found to have a higher ratio of tributyrin activity to triolein activity (a lower SLU/LU ratio) than the parent enzyme:

SPIRPRP(-E) (SEQ ID NO. 22)+E99K+R195Q+R209E+Q249R
N101R+R195Q+R209E+L259S+Y261D
N101R+R195Q+R209E+L259S
N101R+L259S+Y261D
N101R+L259S
Y261D
L259S
SPIRPRP(-E) (SEQ ID NO. 22)+E99K+N101R+Q249R
G263D+L264+I265N+G266E+T267GS
Y261I
D234R
Y261K

The following variants of the parent lipase from *Humicola lanuginosa* may also have a higher ratio of tributyrin activity to triolein activity:

N101R,R195Q,R209E,L259S,Y261D
N101R,R195Q,R209E,L259S
N101R,L259S,Y261D
N101R,L259S

Example 11

Variants of *Fusarium* Lipase with Increased Specificity for Short-Chain Fatty Acids Variants of the parent lipase from *Fusarium oxysporum* were prepared and tested as in the previous example. The following variants were found to have a higher ratio of tributyrin activity to triolein activity than the parent enzyme:

Y23W
Y260D
Y260R
Y260C
Y260N

Example 12

Variants of *Rhizomucor* Lipase with Increased Specificity for Short-Chain Fatty Acids The following variants of the parent lipase from *Rhizomucor miehei* may have an increased specificity for short-chain fatty acids:

Y260C
Y260G
Y260V

Example 13

Variants of *Humicola* Lipase with DGDGase Activity

Variants of the parent lipase from *Humicola lanuginosa* were prepared, and the hydrolytic activity towards DGDG (di-galactosyl-di-glyceride) was determined as described above. The following variants were found to have DGDGase activity, whereas the parent lipase gave a negative result.

D96W+G263Q+L264A+I265T+G266D+T267A
G263Q+L264A+I265T+G266D+T267A
D96W+G263Q+L264A+I265T+G266D+T267A+L269N+270AGGFS
G91A+D96W+E99K+G263Q+L264A+I265T+G266D+T267A+L269N+270AGGFS D96F+G266S

Example 14

Variants of *Humicola* Lipase with Increased pH Optimum

Variants of the parent lipase from *Humicola lanuginosa* were prepared, and the lipase activity was measured by the LU method at pH 7 and 9. The following variants were found to have a higher ratio of activity at pH 9 to activity at pH 7 than the parent lipase:

R84L
R84W
Y21I
Y21V
Y261I

Example 15

Variants of *Humicola* Lipase with Decreased pH Optimum

Variants of the parent lipase from *Humicola lanuginosa* were prepared, and the lipase activity was measured by the LU method at pH 7 and 9. The following variants were found to have a lower ratio of activity at pH 9 to activity at pH 7 than the parent lipase:

Y261D
G266D/E
Y261W

Example 16

Use of *Humicola* Lipase Variants in Degumming of Vegetable Oil

Rapeseed oil was treated with two variants of the lipase from *Humicola lanuginosa*, essentially as described in Example 6 of WO 98/18912 (Novo Nordisk).

One variant was tested at an enzyme dosage of 0.6 mg of enzyme protein per kg of oil. Results of tests at various pH and temperatures showed optimum performance at pH 5.7, 35-45° C., where a final P content of 4 ppm was reached. A separate experiment at 45° C., pH 6 showed that a final P content of 4 ppm could be reached at an enzyme dosage as low as 0.15 mg/kg.

A similar experiment with another *Humicola lanuginosa* lipase variant showed optimum performance at 40° C., pH 5.0-5.5. The enzyme dosage was 0.3 mg/kg.

A degumming experiment was made with a third *Humicola lanuginosa* lipase variant, using rape seed oil at 45° C., pH 5, 1.8 mg enzyme/kg oil. For comparison, a similar experiment was made with the parent lipase (*Humicola lanuginosa* lipase) at 18 mg/kg. The results showed that good degumming (<10 ppm residual P content) was obtained in 3.4 hours with the variant.

The parent lipase (*Humicola lanuginosa* lipase) was found to have very little degumming effect, even at 10 times higher enzyme dosage.

Example 17

Use of Lipase Variants in Baking

A variant of the lipase from *Humicola lanuginosa* was evaluated in baking tests as follows.

Doughs were prepared from Meneba flour according to the European straight dough method (ABF-SP-1201.01) with 40 ppm of ascorbic acid. Various combinations of additives at the following dosages were used: the lipase variant at 0, 0.25, 0.5 or 1.5 mg/kg; phospholipid (lecithin) at 0 or 10 g/kg; and endo-amylase at 0 or 750 MANU/kg.

The endo-amylase was maltogenic amylase from *B. stearothermophilus* (tradename Novamyl®). One MANU (Maltogenic Amylase Novo Unit) is defined as the amount of enzyme required to release one ☐mol of maltose per minute at a concentration of 10 mg of maltotriose substrate per ml of 0.1 M citrate buffer, pH 5.0 at 37 ⚲ C for 30 minutes.

After baking, the loaves were cooled, and the loaf volume, crumb firmness and softness were evaluated after approximately 2 hours. The evaluation was repeated after 1, 3 and 7 days storage at 22° C. wrapped in double plastic bags.

Firmness of crumb was measured using a texture analyzer TA-XT2 from Stable Micro Systems (probe diameter 40 mm).

Softness in gram was measured as the force needed to press a probe 6.25 mm into a crumb of a 25 mm thick slice of bread (25% penetration).

The results showed that the addition of 1.5 mg of the variant increased the loaf volume. The results for firmness and elasticity show that the variant gives significantly softer crumb and significantly better elasticity from day 0 to day 7.

Example 18

Use of Lipase Variants for Dough Stability in Baking

A variant of the *Humicola lanuginosa* lipase was evaluated in a baking trial to evaluate its tolerance towards extended proofing of the dough.

Doughs were prepared from Pelikan flour according to the European straight dough method (347-SP-1217) with 30 ppm ascorbic acid, fungal☐-amylase (10 FAU of Fungamyl), and pentosanase (100 FXU of Pentopan Mono). Dosages of 0.2, 0.4, and 0.6 mg enzyme protein/kg flour of the variant were compared with 1000 LU of the parent lipase.

The doughs were made into rolls. Half of the rolls were proofed for 45 minutes (normal proofing) and the other half for 70 minutes (over proofing).

After baking the bread was cooled, and the volume and the standing of the rolls were evaluated after approximately 2 hours. The standing is a measure of the shape of the rolls and is defined as the height of 10 rolls divided by the width of 10 rolls, which means that nice round loaves have a high standing value, whereas flat rolls have a low standing value.

The results showed that at normal proofing time the volume of 0.4 and 0.6 mg of the variant were better than that of the parent lipase, and the standing of the rolls were better for the variant at all dosages than for the parent lipase. When the rolls were over proofed, both volume and standing was better for the variant at all dosages than for the parent lipase.

Example 19

Effect of Lipase Variants on Off-Odor Development

The development of off-odor from lipases with different chain-length specificity was evaluated in whole milk. The developed butyric acid/sour odor was evaluated by sniffing the samples after heating.

25 ml whole milk was placed in 100 ml blue cap flasks (with caps) in a 32° C. water bath. Of each of the lipases listed below, 0.2 mg enzyme protein per liter milk was added to the flasks. The temperature was raised to 45° C., and evaluation took place after 15 and 105 minutes.

The lipases tested were *Humicola lanuginosa* lipase and variants thereof. For each lipase, the chain-length specificity is expressed as the ratio of activities on triolein (SLU) and tributyrin (LU).

Three persons evaluated the samples and agreed on the ranking shown below

+Detectable smell
++Clear and characteristic butyric acid and/or sour odor
+++Strong butyric acid and/or sour odor Three variants of *Humicola lanuginosa* lipase having a higher SLU/LU ratio than *Humicola lanuginosa* lipase were found to have less malodor than the parent lipase.

Example 20

Effect of Lipase Variants on Malodour on Textile after Washing

Soiling:

Cotton textile was soiled with a dairy product as described here. 50 mg of butter was applied over an area of approximately 30 $cm^2$ in an even spot. The soiled textile was aged for 24 hours at ambient conditions.

Washing Procedure:

Washing of the soiled textile was done in a Terg-O-tometer using a commercial detergent (5 g/l) with and without lipase (1250 and 5000 LU/l). The washing was done at 30° C. for 20 min at 100 rpm. After washing the swatches were left overnight to dry at ambient conditions.

Sensory Analysis:

Next day, the malodour was assessed by a sensory panel consisting of at least 10 trained assessors. Samples were kept in tight glass jars and left at least 30 minutes between every evaluation for accumulation of malodour. Swatches were taken out and the malodour assessed on the textile. The butyric acid malodour was scored according to the scale below. As a reference the sample washed without lipase was used.

0. Fainter smell than reference
1. Same as reference
2. Slightly stronger than reference
3. Definitely stronger than reference
4. Stronger than 3.

Variants of *Humicola lanuginosa* lipase with an increased ratio of triolein/tributyrin activities (increased SLU/LU ratio) were found to give a fainter smell from butter stains than the parent enzyme (*Humicola lanuginosa* lipase). A separate washing experiment showed that the variants, like the parent enzyme, were effective in the removal of lard stains.

Alternative Methods

The intensity of butyric acid from dairy stains on fabric can also be evaluated by instrumental analysis:

1. By Head Space Gas Chromatography, or
2. By extraction of the odours from fabric followed by Gas Chromatography

Example 21

Effect of Lipase Variants on Odour of Bread Baked with Butter

Six variants of the lipase from *Humicola lanuginosa* were prepared and were evaluated in bread baked by the European straight dough procedure (347-SP-1217) with addition of 3% butter. 0.2 mg enzyme protein/kg flour was used for each of the variants.

The chain-length specificity of the variants was also determined by measuring the triolein/tributyrin activity ratio (SLU/LU described above). The parent lipase from *Humicola lanuginosa* and a prior-art lipase with phospholipase acivity from *Fusarium oxysporum* were also tested for comparison.

The results are summarized below:

|  | SLU/LU | Rating |
|---|---|---|
| Variants of the | 2.7 | (+) |
|  | 3 | no effect |

-continued

|  | SLU/LU | Rating |
|---|---|---|
| invention | 7 | no effect |
|  | 28 | no effect |
|  | 70 | no effect |
| Parent lipase | 1.2 | ++ |
| Prior-art lipase | 1.1 | +++ |
| Control (no lipase) | — | no effect |

+ detectable smell
++ clear and characteristic butyric acid and/or sour odour
+++ strong butyric acid and/or sour odour The results indicate that that lipase variants with a SLU/LU ratio at 3 or above (i.e. a high specificity for long-chain fatty acids) give no unpleasant odour in bread baking even with butter in the recipe.

The invention claimed is:

1. A lipolytic enzyme variant which:
   a) comprises an amino acid sequence having at least 95% homology with a parent lipolytic enzyme of the Humicola family;
   b) compared to the parent lipolytic enzyme comprises a substitution to G266A,C,D,N,L,I,S,T,P,V at a position corresponding to position G266 of SEQ ID NO: 32; and
   c) has an increased activity on an ester bond in a substrate compared with the parent lipolytic enzyme wherein the activity is phospholipase activity; digalactosyl-diglyceride activity; or activity on short- or long-chain triglycerides.

2. The variant of claim 1, which further comprises an alteration which is a substitution, a deletion or an insertion at a position corresponding to any of positions 22, 56-59, 61, 64, 83, 85, 91, 94, 249, 255 or 259 of SEQ ID NO: 32.

3. The variant of claim 2, wherein the alteration is a substitution at a position corresponding to position S83T, G91A, N94D, D96S,W,F,G, Q249R or L259N,R,S,M,Q of SEQ ID NO: 32.

4. The variant of claim 2, wherein the alteration is a substitution at a position corresponding to D62A,G,V, K98D, E99K, P256T, G263A and/or I265T,G,V of SEQ ID NO: 32.

5. The variant of claim 2, wherein the parent lipolytic enzyme is the lipase of SEQ ID NO: 32 from *Humicola lanuginosa*.

6. The variant of claim 1, wherein the parent lipolytic enzyme is the lipase of SEQ ID NO: 34 from *Fusarium oxysporum*.

7. The variant of claim 1, wherein the altered activity is a lower activity towards a $C_4$-$C_8$ acyl bond in a triglyceride, or a lower ratio of activity towards a $C_4$-$C_8$ acyl bond in a triglyceride and a $C_{16}$-$C_{20}$ acyl bond in a triglyceride.

8. The variant of claim 7, which comprises an alteration at a position corresponding to position Y21, E56, D57, V60, G61, D62, R81, S83, L259, or Y261 of SEQ ID NO: 32.

9. The variant of claim 7, which comprises a substitution at a position corresponding to Y21V/I, V60G, D62E/A/V, S83T or R84K/L/W of SEQ ID NO: 32.

10. The variant of claim 1, wherein the altered activity is a higher phospholipase activity.

11. The variant of claim 10, which comprises an alteration at a position corresponding to position R81, R84, S85, G263, L264, I265, T267 or L269 of SEQ ID NO: 32.

12. The variant of claim 10, which comprises a substitution at a position corresponding to G263A,E,Q,R; L264A,C,P,Q; I265L,N,T; T267A,Q or L269N of SEQ ID NO: 32.

13. The variant of claim 10, which further comprises a peptide extension at the C-terminal.

14. The variant of claim 13, which comprises a peptide extension of 1-5 amino acid residues at the C-terminal.

15. The variant of claim 13, wherein the peptide extension comprises A, P or D as a first amino acid of the peptide extension.

16. The variant of claim 13, wherein the peptide extension comprises V, G or R as a second amino acid of the peptide extension.

17. The variant of claim 13, wherein the peptide extension comprises V, G or R as a third amino acid of the peptide extension.

18. The variant of claim 13, wherein the peptide extension comprises F as a fourth amino acid of the peptide extension.

19. The variant of claim 13, wherein the peptide extension comprises S as a fifth amino acid of the peptide extension.

20. The variant of claim 1, which further comprises a peptide extension at the C-terminal, wherein the peptide extension comprises S as a fifth amino acid of the peptide extension.

21. The variant of claim 20, further comprising a C-terminal extension of WRRYRSAESVDKRATMTDAELE-KKLNSYVQMDKEYVKNNQARS (SEQ ID NO: 24) in full or truncated form.

22. The variant of claim 1, wherein the altered activity is a higher hydrolytic activity on a digalactosyl-diglyceride.

23. The variant of claim 22, which comprises an amino acid alteration at a position corresponding to a position Y21, G23, N26, D57, D62, R81, S83, S85, T267 or L269 of SEQ ID NO: 32.

24. The variant of claim 23, which comprises two or more such alterations.

25. The variant of claim 23, further comprising at least one alteration in the lid region of the parent lipolytic enzyme.

26. The variant of claim 25, wherein the alteration in the lid region is a substitution of a negatively charged amino acid residue with a neutral or positively charged amino acid residue, or a substitution of a neutral amino acid residue with a positively charged amino residue.

27. The variant of claim 25, which comprises an alteration in the lid region at a position corresponding to position G91, D96 and/or E99 of SEQ ID NO: 32.

28. The variant of claim 25, which comprises a substitution at a position corresponding to a position G91A, D96S,W,F or E99K of SEQ ID NO: 32.

29. The variant of claim 1, which is a variant of a SEQ ID NO: 32 comprising the alterations E1E,D,A+G91G,A,S,T+N94N,D+D96D,G,F,W+E99E,K+G225G,R,K+G263Q,N+L264L,A,V+I265I,T,S+G266G,A,V,S,D,E+T267T,A,V+L269L,I,N,Q.

30. The variant of claim 1, which further comprises SPIRR (SEQ ID NO: 21) as a peptide extension at the N-terminal and/or AGGF (SEQ ID NO: 18) or AGGFS (SEQ ID NO: 19) as a peptide extension at the C-terminal.

31. The variant of claim 1, having phospholipase and galactolipase activity.

32. A recombinant DNA sequence encoding the variant of claim 1.

33. A vector comprising the DNA sequence of claim 32.

34. A transformed host cell harboring the DNA sequence of claim 32.

35. A method of producing a lipolytic enzyme variant comprising
  a) cultivating the cell of claim 34 to express the enzyme; and
  b) recovering the lipolytic enzyme.

36. A process for preparing a dough or baked product prepared from the dough comprising adding the lipolytic enzyme of claim 1 to the dough.

* * * * *

SEQUENCE LISTING

<160> NUMBER OF SEQ ID NOS: 34

<210> SEQ ID NO 1
<211> LENGTH: 24
<212> TYPE: DNA
<213> ORGANISM: Artificial Sequence
<220> FEATURE:
<223> OTHER INFORMATION: Synthetic construct

<400> SEQUENCE: 1
tcaagaatag ttcaaacaag aaga                                          24

<210> SEQ ID NO 2
<211> LENGTH: 24
<212> TYPE: DNA
<213> ORGANISM: Artificial Sequence
<220> FEATURE:
<223> OTHER INFORMATION: Primer

<400> SEQUENCE: 2
ggttgtctaa ctccttcctt ttcg                                          24

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
tgtcccymgw ctccckcck                                                19

<210> SEQ ID NO 4
<211> LENGTH: 27
<212> TYPE: DNA
<213> ORGANISM: Artificial Sequence
<220> FEATURE:
<223> OTHER INFORMATION: Primer

<400> SEQUENCE: 4
gaagtamyry agrtgmgcag sratatc                                       27

<210> SEQ ID NO 5
<211> LENGTH: 27
<212> TYPE: DNA
<213> ORGANISM: Artificial Sequence
<220> FEATURE:
<223> OTHER INFORMATION: Primer -continued

```
<400> SEQUENCE: 5
gatatysctg ckcayctryr ktacttc                                      27

<210> SEQ ID NO 6
<211> LENGTH: 23
<212> TYPE: DNA
<213> ORGANISM: Artificial Sequence
<220> FEATURE:
<223> OTHER INFORMATION: Primer

<400> SEQUENCE: 6
cggaatgtta ggctggttat tgc                                          23

<210> SEQ ID NO 7
<211> LENGTH: 20
<212> TYPE: DNA
<213> ORGANISM: Artificial Sequence
<220> FEATURE:
<223> OTHER INFORMATION: Primer

<400> SEQUENCE: 7
cttttcggtt agagcggatg                                              20

<210> SEQ ID NO 8
<211> LENGTH: 120
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (59)..(59)
<223> OTHER INFORMATION: n = a,t,c, or g
<220> FEATURE:
<221> NAME/KEY: misc_feature
<222> LOCATION: (60)..(60)
<223> OTHER INFORMATION: n = a,t,c, or g
<220> FEATURE:
<221> NAME/KEY: misc_feature
<222> LOCATION: (62)..(62)
<223> OTHER INFORMATION: n = a,t,c, or g
<220> FEATURE:
<221> NAME/KEY: misc_feature
<222> LOCATION: (63)..(63)
<223> OTHER INFORMATION: n = a,t,c, or g
<220> FEATURE:
<221> NAME/KEY: misc_feature
<222> LOCATION: (65)..(65)
<223> OTHER INFORMATION: n = a,t,c, or g
<220> FEATURE:
<221> NAME/KEY: misc_feature
<222> LOCATION: (66)..(66)
<223> OTHER INFORMATION: n = a,t,c, or g
<220> FEATURE:
<221> NAME/KEY: misc_feature
<222> LOCATION: (68)..(68)
<223> OTHER INFORMATION: n = a,t,c, or g
<220> FEATURE:
<221> NAME/KEY: misc_feature
<222> LOCATION: (69)..(69)
<223> OTHER INFORMATION: n = a,t,c, or g
<220> FEATURE:
<221> NAME/KEY: misc_feature
<222> LOCATION: (74)..(74)
<223> OTHER INFORMATION: n = a,t,c, or g
<220> FEATURE:
<221> NAME/KEY: misc_feature
<222> LOCATION: (75)..(75)
<223> OTHER INFORMATION: n = a,t,c, or g
<220> FEATURE:
<221> NAME/KEY: misc_feature
<222> LOCATION: (77)..(77)
<223> OTHER INFORMATION: n = a,t,c, or g
```

```
<220> FEATURE:
<221> NAME/KEY: misc_feature
<222> LOCATION: (78)..(78)
<223> OTHER INFORMATION: n = a,t,c, or g
<220> FEATURE:
<221> NAME/KEY: misc_feature
<222> LOCATION: (80)..(80)
<223> OTHER INFORMATION: n = a,t,c, or g
<220> FEATURE:
<221> NAME/KEY: misc_feature
<222> LOCATION: (81)..(81)
<223> OTHER INFORMATION: n = a,t,c, or g
<220> FEATURE:
<221> NAME/KEY: misc_feature
<222> LOCATION: (83)..(83)
<223> OTHER INFORMATION: n = a,t,c, or g
<220> FEATURE:
<221> NAME/KEY: misc_feature
<222> LOCATION: (84)..(84)
<223> OTHER INFORMATION: n = a,t,c, or g

<400> SEQUENCE: 8
gtaagcgtga cataactaat tacatcatgc ggccctctag agtcgaccca gccgctamnn    60
wnnwnnsnnc wawnnsnnmn nwnntdscbs gaagtaccat aggtgcgcag bgatatccgg   120

<210> SEQ ID NO 9
<211> LENGTH: 118
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (71)..(71)
<223> OTHER INFORMATION: n = a,t,c, or g
<220> FEATURE:
<221> NAME/KEY: misc_feature
<222> LOCATION: (72)..(72)
<223> OTHER INFORMATION: n = a,t,c, or g
<220> FEATURE:
<221> NAME/KEY: misc_feature
<222> LOCATION: (74)..(74)
<223> OTHER INFORMATION: n = a,t,c, or g
<220> FEATURE:
<221> NAME/KEY: misc_feature
<222> LOCATION: (75)..(75)
<223> OTHER INFORMATION: n = a,t,c, or g
<220> FEATURE:
<221> NAME/KEY: misc_feature
<222> LOCATION: (77)..(77)
<223> OTHER INFORMATION: n = a,t,c, or g
<220> FEATURE:
<221> NAME/KEY: misc_feature
<222> LOCATION: (78)..(78)
<223> OTHER INFORMATION: n = a,t,c, or g
<220> FEATURE:
<221> NAME/KEY: misc_feature
<222> LOCATION: (79)..(79)
<223> OTHER INFORMATION: n = a,t,c, or g
<220> FEATURE:
<221> NAME/KEY: misc_feature
<222> LOCATION: (81)..(81)
<223> OTHER INFORMATION: n = a,t,c, or g
<220> FEATURE:
<221> NAME/KEY: misc_feature
<222> LOCATION: (82)..(82)
<223> OTHER INFORMATION: n = a,t,c, or g

<400> SEQUENCE: 9
gtaagcgtga cataactaat tacatcatgc ggccctctag agtcgaccca gccgcgccgc    60
gcactacwaw nnsnnmnnnw nntdscbsga agtaccatag gtgcgcagbg atatccgg    118

<210> SEQ ID NO 10
<211> LENGTH: 120
```

```
<212> TYPE: DNA
<213> ORGANISM: Artificial Sequence
<220> FEATURE:
<223> OTHER INFORMATION: Primer
<220> FEATURE:
<221> NAME/KEY: misc_feature
<222> LOCATION: (59)..(59)
<223> OTHER INFORMATION: n= a,t,c,g
<220> FEATURE:
<221> NAME/KEY: misc_feature
<222> LOCATION: (60)..(60)
<223> OTHER INFORMATION: n= a,t,c,g
<220> FEATURE:
<221> NAME/KEY: misc_feature
<222> LOCATION: (62)..(62)
<223> OTHER INFORMATION: n= a,t,c,g
<220> FEATURE:
<221> NAME/KEY: misc_feature
<222> LOCATION: (63)..(63)
<223> OTHER INFORMATION: n= a,t,c,g
<220> FEATURE:
<221> NAME/KEY: misc_feature
<222> LOCATION: (65)..(65)
<223> OTHER INFORMATION: n= a,t,c,g
<220> FEATURE:
<221> NAME/KEY: misc_feature
<222> LOCATION: (66)..(66)
<223> OTHER INFORMATION: n= a,t,c,g
<220> FEATURE:
<221> NAME/KEY: misc_feature
<222> LOCATION: (68)..(68)
<223> OTHER INFORMATION: n= a,t,c,g
<220> FEATURE:
<221> NAME/KEY: misc_feature
<222> LOCATION: (69)..(69)
<223> OTHER INFORMATION: n= a,t,c,g
<220> FEATURE:
<221> NAME/KEY: misc_feature
<222> LOCATION: (71)..(71)
<223> OTHER INFORMATION: n= a,t,c,g
<220> FEATURE:
<221> NAME/KEY: misc_feature
<222> LOCATION: (72)..(72)
<223> OTHER INFORMATION: n= a,t,c,g
<220> FEATURE:
<221> NAME/KEY: misc_feature
<222> LOCATION: (74)..(74)
<223> OTHER INFORMATION: n= a,t,c,g
<220> FEATURE:
<221> NAME/KEY: misc_feature
<222> LOCATION: (75)..(75)
<223> OTHER INFORMATION: n= a,t,c,g
<220> FEATURE:
<221> NAME/KEY: misc_feature
<222> LOCATION: (77)..(77)
<223> OTHER INFORMATION: n= a,t,c,g
<220> FEATURE:
<221> NAME/KEY: misc_feature
<222> LOCATION: (78)..(78)
<223> OTHER INFORMATION: n= a,t,c,g
<220> FEATURE:
<221> NAME/KEY: misc_feature
<222> LOCATION: (80)..(80)
<223> OTHER INFORMATION: n= a,t,c,g
<220> FEATURE:
<221> NAME/KEY: misc_feature
<222> LOCATION: (81)..(81)
<223> OTHER INFORMATION: n= a,t,c,g
<220> FEATURE:
<221> NAME/KEY: misc_feature
<222> LOCATION: (83)..(83)
<223> OTHER INFORMATION: n= a,t,c,g
<220> FEATURE:
<221> NAME/KEY: misc_feature
<222> LOCATION: (84)..(84)
<223> OTHER INFORMATION: n= a,t,c,g

<400> SEQUENCE: 10
gtaagcgtga cataactaat tacatcatgc ggccctctag agtcgaccca gccgctamnn    60
```

-continued wnnwnnsnns nnwnnsnnmn nwnntdscbs gaagtaccat aggtgcgcag bgatatccgg    120

<210> SEQ ID NO 11
<211> LENGTH: 82
<212> TYPE: DNA
<213> ORGANISM: Artificial Sequence
<220> FEATURE:
<223> OTHER INFORMATION: Primer

<400> SEQUENCE: 11
gtaagcgtga cataactaat tacatcatgc ggccctctag agtcgaccca gccgctagtt    60
acaggcgtca gtcgcctgga ag    82

<210> SEQ ID NO 12
<211> LENGTH: 82
<212> TYPE: DNA
<213> ORGANISM: Artificial Sequence
<220> FEATURE:
<223> OTHER INFORMATION: Primer

<400> SEQUENCE: 12
gtaagcgtga cataactaat tacatcatgc ggccctctag agtcgaccca gccgctaagc    60
gttacaggcg tcagtcgcct gg    82

<210> SEQ ID NO 13
<211> LENGTH: 82
<212> TYPE: DNA
<213> ORGANISM: Artificial Sequence
<220> FEATURE:
<223> OTHER INFORMATION: Primer

<400> SEQUENCE: 13
gtaagcgtga cataactaat tacatcatgc ggccctctag agtcgaccca gccgctaacc    60
agcgttacag gcgtcagtcg cc    82

<210> SEQ ID NO 14
<211> LENGTH: 82
<212> TYPE: DNA
<213> ORGANISM: Artificial Sequence
<220> FEATURE:
<223> OTHER INFORMATION: Primer

<400> SEQUENCE: 14
gtaagcgtga cataactaat tacatcatgc ggccctctag agtcgaccca gccgctagcc    60
accagcgtta caggcgtcag tc    82

<210> SEQ ID NO 15
<211> LENGTH: 4
<212> TYPE: PRT
<213> ORGANISM: Artificial Sequence
<220> FEATURE:
<223> OTHER INFORMATION: Synthetic

<400> SEQUENCE: 15

Pro Val Gly Phe
1

<210> SEQ ID NO 16
<211> LENGTH: 4
<212> TYPE: PRT
<213> ORGANISM: Artificial Sequence
<220> FEATURE:
<223> OTHER INFORMATION: Synthetic

```
<400> SEQUENCE: 16

Ala Gly Arg Phe
1

<210> SEQ ID NO 17
<211> LENGTH: 4
<212> TYPE: PRT
<213> ORGANISM: Artificial Sequence
<220> FEATURE:
<223> OTHER INFORMATION: Synthetic

<400> SEQUENCE: 17

Pro Arg Gly Phe
1

<210> SEQ ID NO 18
<211> LENGTH: 4
<212> TYPE: PRT
<213> ORGANISM: Artificial Sequence
<220> FEATURE:
<223> OTHER INFORMATION: Synthetic

<400> SEQUENCE: 18

Ala Gly Gly Phe
1

<210> SEQ ID NO 19
<211> LENGTH: 5
<212> TYPE: PRT
<213> ORGANISM: Artificial Sequence
<220> FEATURE:
<223> OTHER INFORMATION: Synthetic

<400> SEQUENCE: 19

Ala Gly Gly Phe Ser
1               5

<210> SEQ ID NO 20
<211> LENGTH: 48
<212> TYPE: PRT
<213> ORGANISM: Artificial Sequence
<220> FEATURE:
<223> OTHER INFORMATION: Synthetic

<400> SEQUENCE: 20

Ala Gly Gly Phe Ser Trp Arg Arg Tyr Arg Ser Ala Glu Ser Val Asp
1               5                   10                  15

Lys Arg Ala Thr Met Thr Asp Ala Glu Leu Glu Lys Lys Leu Asn Ser
            20                  25                  30

Tyr Val Gln Met Asp Lys Glu Tyr Val Lys Asn Asn Gln Ala Arg Ser
        35                  40                  45

<210> SEQ ID NO 21
<211> LENGTH: 5
<212> TYPE: PRT
<213> ORGANISM: Artificial Sequence
<220> FEATURE:
<223> OTHER INFORMATION: Synthetic

<400> SEQUENCE: 21

Ser Pro Ile Arg Arg
1               5

<210> SEQ ID NO 22
<211> LENGTH: 7
<212> TYPE: PRT
```

```
<213> ORGANISM: Artificial Sequence
<220> FEATURE:
<223> OTHER INFORMATION: Synthetic

<400> SEQUENCE: 22

Ser Pro Ile Arg Pro Arg Pro
1               5

<210> SEQ ID NO 23
<211> LENGTH: 6
<212> TYPE: PRT
<213> ORGANISM: Artificial Sequence
<220> FEATURE:
<223> OTHER INFORMATION: Synthetic

<400> SEQUENCE: 23

Ser Pro Pro Arg Arg Pro
1               5

<210> SEQ ID NO 24
<211> LENGTH: 43
<212> TYPE: PRT
<213> ORGANISM: Artificial Sequence
<220> FEATURE:
<223> OTHER INFORMATION: Synthetic

<400> SEQUENCE: 24

Trp Arg Arg Tyr Arg Ser Ala Glu Ser Val Asp Lys Arg Ala Thr Met
1               5                   10                  15

Thr Asp Ala Glu Leu Glu Lys Lys Leu Asn Ser Tyr Val Gln Met Asp
            20                  25                  30

Lys Glu Tyr Val Lys Asn Asn Gln Ala Arg Ser
        35                  40

<210> SEQ ID NO 25
<211> LENGTH: 8
<212> TYPE: PRT
<213> ORGANISM: Artificial Sequence
<220> FEATURE:
<223> OTHER INFORMATION: Synthetic

<400> SEQUENCE: 25

Ser Pro Pro Cys Gly Arg Arg Pro
1               5

<210> SEQ ID NO 26
<211> LENGTH: 7
<212> TYPE: PRT
<213> ORGANISM: Artificial Sequence
<220> FEATURE:
<223> OTHER INFORMATION: Synthetic

<400> SEQUENCE: 26

Ser Pro Cys Arg Pro Arg Pro
1               5

<210> SEQ ID NO 27
<211> LENGTH: 21
<212> TYPE: DNA
<213> ORGANISM: Artificial Sequence
<220> FEATURE:
<223> OTHER INFORMATION: Primer

<400> SEQUENCE: 27
agaaatcggg tatcctttca g                                           21
```

```
<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
gaatgacttg gttgacgcgt caccagtcac                                      30

<210> SEQ ID NO 29
<211> LENGTH: 26
<212> TYPE: DNA
<213> ORGANISM: Artificial Sequence
<220> FEATURE:
<223> OTHER INFORMATION: Primer

<400> SEQUENCE: 29
tctagcccag aatactggat caaatc                                          26

<210> SEQ ID NO 30
<211> LENGTH: 269
<212> TYPE: PRT
<213> ORGANISM: Rhizomucor miehei

<400> SEQUENCE: 30
```

Ser Ile Asp Gly Gly Ile Arg Ala Ala Thr Ser Gln Glu Ile Asn Glu
1               5                   10                  15

Leu Thr Tyr Tyr Thr Thr Leu Ser Ala Asn Ser Tyr Cys Arg Thr Val
            20                  25                  30

Ile Pro Gly Ala Thr Trp Asp Cys Ile His Cys Asp Ala Thr Glu Asp
        35                  40                  45

Leu Lys Ile Ile Lys Thr Trp Ser Thr Leu Ile Tyr Asp Thr Asn Ala
    50                  55                  60

Met Val Ala Arg Gly Asp Ser Glu Lys Thr Ile Tyr Ile Val Phe Arg
65                  70                  75                  80

Gly Ser Ser Ser Ile Arg Asn Trp Ile Ala Asp Leu Thr Phe Val Pro
                85                  90                  95

Val Ser Tyr Pro Pro Val Ser Gly Thr Lys Val His Lys Gly Phe Leu
            100                 105                 110

Asp Ser Tyr Gly Glu Val Gln Asn Glu Leu Val Ala Thr Val Leu Asp
        115                 120                 125

Gln Phe Lys Gln Tyr Pro Ser Tyr Lys Val Ala Val Thr Gly His Ser
    130                 135                 140

Leu Gly Gly Ala Thr Ala Leu Leu Cys Ala Leu Asp Leu Tyr Gln Arg
145                 150                 155                 160

Glu Glu Gly Leu Ser Ser Ser Asn Leu Phe Leu Tyr Thr Gln Gly Gln
                165                 170                 175

Pro Arg Val Gly Asp Pro Ala Phe Ala Asn Tyr Val Val Ser Thr Gly
            180                 185                 190

Ile Pro Tyr Arg Arg Thr Val Asn Glu Arg Asp Ile Val Pro His Leu
        195                 200                 205

Pro Pro Ala Ala Phe Gly Phe Leu His Ala Gly Glu Glu Tyr Trp Ile
    210                 215                 220

Thr Asp Asn Ser Pro Glu Thr Val Gln Val Cys Thr Ser Asp Leu Glu
225                 230                 235                 240

Thr Ser Asp Cys Ser Asn Ser Ile Val Pro Phe Thr Ser Val Leu Asp
                245                 250                 255

His Leu Ser Tyr Phe Gly Ile Asn Thr Gly Leu Cys Thr
            260                 265

-continued

```
<210> SEQ ID NO 31
<211> LENGTH: 269
<212> TYPE: PRT
<213> ORGANISM: Rhizopus delemar

<400> SEQUENCE: 31

Ser Asp Gly Gly Lys Val Val Ala Ala Thr Thr Ala Gln Ile Gln Glu
1               5                   10                  15

Phe Thr Lys Tyr Ala Gly Ile Ala Ala Thr Ala Tyr Cys Arg Ser Val
            20                  25                  30

Val Pro Gly Asn Lys Trp Asp Cys Val Gln Cys Gln Lys Trp Val Pro
        35                  40                  45

Asp Gly Lys Ile Ile Thr Thr Phe Thr Ser Leu Leu Ser Asp Thr Asn
    50                  55                  60

Gly Tyr Val Leu Arg Ser Asp Lys Gln Lys Thr Ile Tyr Leu Val Phe
65                  70                  75                  80

Arg Gly Thr Asn Ser Phe Arg Ser Ala Ile Thr Asp Ile Val Phe Asn
                85                  90                  95

Phe Ser Asp Tyr Lys Pro Val Lys Gly Ala Lys Val His Ala Gly Phe
            100                 105                 110

Leu Ser Ser Tyr Glu Gln Val Val Asn Asp Tyr Phe Pro Val Val Gln
        115                 120                 125

Glu Gln Leu Thr Ala His Pro Thr Tyr Lys Val Ile Val Thr Gly His
    130                 135                 140

Ser Leu Gly Gly Ala Gln Ala Leu Leu Ala Gly Met Asp Leu Tyr Gln
145                 150                 155                 160

Arg Glu Pro Arg Leu Ser Pro Lys Asn Leu Ser Ile Phe Thr Val Gly
                165                 170                 175

Gly Pro Arg Val Gly Asn Pro Thr Phe Ala Tyr Tyr Val Glu Ser Thr
            180                 185                 190

Gly Ile Pro Phe Gln Arg Thr Val His Lys Arg Asp Ile Val Pro His
        195                 200                 205

Val Pro Pro Gln Ser Phe Gly Phe Leu His Pro Gly Val Glu Ser Trp
    210                 215                 220

Ile Lys Ser Gly Thr Ser Asn Val Gln Ile Cys Thr Ser Glu Ile Glu
225                 230                 235                 240

Thr Lys Asp Cys Ser Asn Ser Ile Val Pro Phe Thr Ser Ile Leu Asp
                245                 250                 255

His Leu Ser Tyr Phe Asp Ile Asn Glu Gly Ser Cys Leu
            260                 265

<210> SEQ ID NO 32
<211> LENGTH: 269
<212> TYPE: PRT
<213> ORGANISM: Thermomyces lanuginosus

<400> SEQUENCE: 32

Glu Val Ser Gln Asp Leu Phe Asn Gln Phe Asn Leu Phe Ala Gln Tyr
1               5                   10                  15

Ser Ala Ala Ala Tyr Cys Gly Lys Asn Asn Asp Ala Pro Ala Gly Thr
            20                  25                  30

Asn Ile Thr Cys Thr Gly Asn Ala Cys Pro Glu Val Glu Lys Ala Asp
        35                  40                  45

Ala Thr Phe Leu Tyr Ser Phe Glu Asp Ser Gly Val Gly Asp Val Thr
    50                  55                  60
```

```
Gly Phe Leu Ala Leu Asp Asn Thr Asn Lys Leu Ile Val Leu Ser Phe
 65                  70                  75                  80

Arg Gly Ser Arg Ser Ile Glu Asn Trp Ile Gly Asn Leu Asn Phe Asp
                 85                  90                  95

Leu Lys Glu Ile Asn Asp Ile Cys Ser Gly Cys Arg Gly His Asp Gly
            100                 105                 110

Phe Thr Ser Ser Trp Arg Ser Val Ala Asp Thr Leu Arg Gln Lys Val
        115                 120                 125

Glu Asp Ala Val Arg Glu His Pro Asp Tyr Arg Val Val Phe Thr Gly
130                 135                 140

His Ser Leu Gly Gly Ala Leu Ala Thr Val Ala Gly Ala Asp Leu Arg
145                 150                 155                 160

Gly Asn Gly Tyr Asp Ile Asp Val Phe Ser Tyr Gly Ala Pro Arg Val
                165                 170                 175

Gly Asn Arg Ala Phe Ala Glu Phe Leu Thr Val Gln Thr Gly Gly Thr
            180                 185                 190

Leu Tyr Arg Ile Thr His Thr Asn Asp Ile Val Pro Arg Leu Pro Pro
        195                 200                 205

Arg Glu Phe Gly Tyr Ser His Ser Ser Pro Glu Tyr Trp Ile Lys Ser
210                 215                 220

Gly Thr Leu Val Pro Val Thr Arg Asn Asp Ile Val Lys Ile Glu Gly
225                 230                 235                 240

Ile Asp Ala Thr Gly Gly Asn Asn Gln Pro Asn Ile Pro Asp Ile Pro
                245                 250                 255

Ala His Leu Trp Tyr Phe Gly Leu Ile Gly Thr Cys Leu
            260                 265

<210> SEQ ID NO 33
<211> LENGTH: 279
<212> TYPE: PRT
<213> ORGANISM: Penicillium camemberti

<400> SEQUENCE: 33

Asp Val Ser Thr Ser Glu Leu Asp Gln Phe Glu Phe Trp Val Gln Tyr
 1               5                  10                  15

Ala Ala Ala Ser Tyr Tyr Glu Ala Asp Tyr Thr Ala Gln Val Gly Asp
                20                  25                  30

Lys Leu Ser Cys Ser Lys Gly Asn Cys Pro Glu Val Glu Ala Thr Gly
            35                  40                  45

Ala Thr Val Ser Tyr Asp Phe Ser Asp Ser Thr Ile Thr Asp Thr Ala
 50                  55                  60

Gly Tyr Ile Ala Val Asp His Thr Asn Ser Ala Val Val Leu Ala Phe
 65                  70                  75                  80

Arg Gly Ser Tyr Ser Val Arg Asn Trp Val Ala Asp Ala Thr Phe Val
                 85                  90                  95

His Thr Asn Pro Gly Leu Cys Asp Gly Cys Leu Ala Glu Leu Gly Phe
            100                 105                 110

Trp Ser Ser Trp Lys Leu Val Arg Asp Asp Ile Ile Lys Glu Leu Lys
        115                 120                 125

Glu Val Val Ala Gln Asn Pro Asn Tyr Glu Leu Val Val Val Gly His
130                 135                 140

Ser Leu Gly Ala Ala Val Ala Thr Leu Ala Ala Thr Asp Leu Arg Gly
145                 150                 155                 160

Lys Gly Tyr Pro Ser Ala Lys Leu Tyr Ala Tyr Ala Ser Pro Arg Val
                165                 170                 175
```

```
Gly Asn Ala Ala Leu Ala Lys Tyr Ile Thr Ala Gln Gly Asn Asn Phe
                180                 185                 190

Arg Phe Thr His Thr Asn Asp Pro Val Pro Lys Leu Pro Leu Leu Ser
            195                 200                 205

Met Gly Tyr Val His Val Ser Pro Glu Tyr Trp Ile Thr Ser Pro Asn
        210                 215                 220

Asn Ala Thr Val Ser Thr Ser Asp Ile Lys Val Ile Asp Gly Asp Val
225                 230                 235                 240

Ser Phe Asp Gly Asn Thr Gly Thr Gly Leu Pro Leu Leu Thr Asp Phe
                245                 250                 255

Glu Ala His Ile Trp Tyr Phe Val Gln Val Asp Ala Gly Lys Gly Pro
            260                 265                 270

Gly Leu Pro Phe Lys Arg Val
            275

<210> SEQ ID NO 34
<211> LENGTH: 316
<212> TYPE: PRT
<213> ORGANISM: Fusarium oxysporum

<400> SEQUENCE: 34

Ala Val Gly Val Thr Thr Thr Asp Phe Ser Asn Phe Lys Phe Tyr Ile
1               5                   10                  15

Gln His Gly Ala Ala Tyr Cys Asn Ser Glu Ala Ala Ala Gly Ser
            20                  25                  30

Lys Ile Thr Cys Ser Asn Asn Gly Cys Pro Thr Val Gln Gly Asn Gly
        35                  40                  45

Ala Thr Ile Val Thr Ser Phe Val Gly Ser Lys Thr Gly Ile Gly Gly
    50                  55                  60

Tyr Val Ala Thr Asp Ser Ala Arg Lys Glu Ile Val Ser Phe Arg
65                  70                  75                  80

Gly Ser Ile Asn Ile Arg Asn Trp Leu Thr Asn Leu Asp Phe Gly Gln
                85                  90                  95

Glu Asp Cys Ser Leu Val Ser Gly Cys Gly Val His Ser Gly Phe Gln
            100                 105                 110

Arg Ala Trp Asn Glu Ile Ser Ser Gln Ala Thr Ala Ala Val Ala Ser
        115                 120                 125

Ala Arg Lys Ala Asn Pro Ser Phe Asn Val Ile Ser Thr Gly His Ser
130                 135                 140

Leu Gly Gly Ala Val Ala Val Leu Ala Ala Ala Asn Leu Arg Val Gly
145                 150                 155                 160

Gly Thr Pro Val Asp Ile Tyr Thr Tyr Gly Ser Pro Arg Val Gly Asn
                165                 170                 175

Ala Gln Leu Ser Ala Phe Val Ser Asn Gln Ala Gly Gly Glu Tyr Arg
            180                 185                 190

Val Thr His Ala Asp Asp Pro Val Pro Arg Leu Pro Pro Leu Ile Phe
        195                 200                 205

Gly Tyr Arg His Thr Thr Pro Glu Phe Trp Leu Ser Gly Gly Gly Gly
    210                 215                 220

Asp Lys Val Asp Tyr Thr Ile Ser Asp Val Lys Val Cys Glu Gly Ala
225                 230                 235                 240

Ala Asn Leu Gly Cys Asn Gly Gly Thr Leu Gly Leu Asp Ile Ala Ala
                245                 250                 255

His Leu His Tyr Phe Gln Ala Thr Asp Ala Cys Asn Ala Gly Gly Phe
            260                 265                 270
```

```
Ser Trp Arg Arg Tyr Arg Ser Ala Glu Ser Val Asp Lys Arg Ala Thr
        275             280             285

Met Thr Asp Ala Glu Leu Glu Lys Lys Leu Asn Ser Tyr Val Gln Met
    290             295             300

Asp Lys Glu Tyr Val Lys Asn Asn Gln Ala Arg Ser
305             310             315
```